United States Patent
Huang et al.

(10) Patent No.: US 9,063,109 B2
(45) Date of Patent: Jun. 23, 2015

(54) POLYANTHRYLENE MATERIALS AND METHODS FOR THEIR PREPARATION AND USE

(71) Applicant: Tongji University, Shanghai (CN)

(72) Inventors: Mei-rong Huang, Shanghai (CN); Shao-jun Huang, Yongzhou (CN); Jiang-Ling Li, Shanghai (CN); Xin-gui Li, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 14/251,396

(22) Filed: Apr. 11, 2014

(65) Prior Publication Data

US 2014/0220695 A1 Aug. 7, 2014

Related U.S. Application Data

(62) Division of application No. 13/505,059, filed as application No. PCT/CN2011/072487 on Apr. 7, 2011, now Pat. No. 8,735,166.

(51) Int. Cl.
| | |
|---|---|
| *G01N 33/20* | (2006.01) |
| *C09K 11/06* | (2006.01) |
| *C08G 61/10* | (2006.01) |
| *C08L 65/00* | (2006.01) |
| *G01N 21/64* | (2006.01) |
| *G01N 33/00* | (2006.01) |

(52) U.S. Cl.
CPC ............... *G01N 33/20* (2013.01); *Y10T 436/21* (2015.01); *Y10T 436/212* (2015.01); *C09K 11/06* (2013.01); *C09K 2211/1416* (2013.01); *C08G 61/10* (2013.01); *C08L 65/00* (2013.01); *G01N 21/643* (2013.01); *C08G 2261/314* (2013.01); *C08G 2261/43* (2013.01); *G01N 2021/6417* (2013.01)

(58) Field of Classification Search
CPC .. C08G 61/10; C08G 2261/43; Y10T 436/21; Y10T 436/212; G01N 2021/6417; G01N 33/20
USPC ................ 436/84; 422/186.3, 82.08; 528/396
See application file for complete search history.

(56) References Cited

U.S. PATENT DOCUMENTS

| | | | |
|---|---|---|---|
| 6,322,910 | B1 | 11/2001 | Arai et al. |
| 2006/0072053 | A1 | 4/2006 | Kathirgamanathan et al. |

(Continued)

FOREIGN PATENT DOCUMENTS

| | | | |
|---|---|---|---|
| CN | 101061199 A | | 10/2007 |
| EP | 1585797 B1 | | 8/2008 |

(Continued)

OTHER PUBLICATIONS

Bricks et al., On the development of sensor molecules that display $Fe^{III}$-amplified fluorescence. *Journal of the American Chemical Society*, 2005, 127(39), 13522-13529.

(Continued)

*Primary Examiner* — Rebecca M Fritchman
(74) *Attorney, Agent, or Firm* — Knobbe, Martens, Olson & Bear LLP

(57) ABSTRACT

Compositions containing polyanthrylene and methods of making these compositions are disclosed herein. The polyanthrylene composition can, for example, be used for detection of iron in a sample.

21 Claims, 8 Drawing Sheets

(56) References Cited

U.S. PATENT DOCUMENTS

| | | | |
|---|---|---|---|
| 2009/0072712 | A1 | 3/2009 | Stoessel et al. |
| 2012/0097938 | A1 | 4/2012 | Meyer et al. |
| 2012/0309095 | A1 | 12/2012 | Huang et al. |

FOREIGN PATENT DOCUMENTS

| | | |
|---|---|---|
| JP | 63-020326 A | 1/1988 |
| JP | 2006-512436 A | 4/2006 |
| WO | WO/2010/149261 | 12/2010 |
| WO | WO2010/149261 A1 | 12/2010 |

OTHER PUBLICATIONS

Cai et al. Atomically precise bottom-up fabrication of grapheme nanoribbons. Nature, 2010, vol. 466, pp. 470-473.

Cha & Park, Determination of iron(III) with salicylic acid by the fluorescence quenching method. *Talanta*, 1998, 46, 1567-1571.

Cui et al. Triphenylamine-Based Fluorescent Conjugated Copolymers with Pendant Terpyridyl Ligands as Chemosensors for Metal Ions, J. Polym. Sci. Part A: Polym. Chem. 2010, 48, 1310-1316.

Demange et al., Structure of azotobactin D, a siderophore of *Azotobacter vinelandii* strain D. *Biochemistry*, 1988, 27: 2745-2752.

Falkowski et al. Biogenochemical controlsand feedbacks on ocean primary production, Science, 1998, 281, 200-206.

Ghosh et al., Epoxy-based polymer bearing 1-naphthylamine units: highly selective fluorescent chemosensor for ferric ion. *Tetrahedron Letters* 2010, 51, 3177-3180.

Hara et al., Electrochemical polymerization of naphthalene using a composite electrolyte of aluminum chloride and copper(I) chloride, Chem. Lett. 1990, 269-272.

Haritash, AK, Kaushik, CP (2009) Biodegradation aspects of polycyclic aromatic hydrocarbons (PAHs): a review. J Hazard Mater 169, 1-15.

Hinterhofer, Poly(9,10-anthrylen)e, Makromol. Chem. 1980, 181, 67-81.

Huang et al., Electrochemical polymerization of naphthalene in the electrolyte of boron trifluoride diethyl etherate containing trifluoroacetic acid and polyethylene glycol oligomer, J. Electroanal. Chem. 2003, 556, 159-165.

Lam et al. Fluorescence-Based Siderophore Biosensor for the Determination of Bioavailable Iron in Oceanic Waters, Anal. Chem. 2006, 78, 5040-5045.

Lee et al., Thin Film Optical Sensors Employing Polyelectrolyte Assembly, Langmuir 2000, 16, 10482-10489.

Lee et al., A novel strategy to selectively detect Fe(III) in aqueous media driven by hydrolysis of a rhodamine 6G Schiff base. *Chem. Commun.*, 2010, 46, 1407-1409.

Li et al., Simple efficient synthesis of strongly luminescent polypyrene with intrinsic conductivity and high carbon yield by chemical oxidative polymerization of pyrene. Chemistry—A European Journal, 2010, 16(16): 4803-4813.

Lohani et al., Facile synthesis of anthracene-appended amino acids as highly selective and sensitive fluorescent Fe3+ ion sensors. Bioorg Med Chem Lett., 2009, 19, 6069-6073.

Lohani et al. The effect of absorbance of Fe3+ on the detection of Fe3+ by fluorescent chemical sensors. Sensors and Actuators B: Chemical; 2010, vol. 143, issue 2, pp. 649-654.

Luo et al., Design, synthesis and properties of novel iron(III)-specific fluorescent probes. *Journal of Pharmacy and Pharmacology*, 2004, 56, 529-536.

Mao et al., An rhodamine-based fluorescence probe for iron(III) ion determination in aqueous solution. *Talanta*, 2010, 80, 2093-2098.

Martin, Glacial-interglacial $CO_2$ change: the iron hypothesis. Palaeoceanography, 1990, 5(1): 1-13.

Moon et al., Aminoxy-linked rhodamine hydroxamate as fluorescent chemosensor for $Fe^{3+}$ in aqueous media, Tetrahedron Lett. 2010, 51, 3290-3293.

Müller et al., Synthesis and characterization of soluble oligo(9,10-anthrylene)s, Chem. Ber. 1994, 127, 437-444.

Müller et al., Novel Oligo(9,IO-anthrylene)s: Models for Electron Transfer and High-Spin Formation, J. Am. Chem. Soc. 1995, 117, 5840-5850.

Palanche et al., Fluorescent siderophore-based chemosensors: iron(III) quantitative determinations. *Journal of Biological Inorganic Chemistry*, 1999, 4(2), 188-198.

Quantichrom Iron Assay Kit, description from BioAssay Systems (Hayward, CA), 2009.

Schopov et al., Conducting polymers with anthracene repeating units, Polymer Communications, 1987, 28, 34-36.

Senthilnithy et al, Fluorescence quenching and bonding properties of some hydroxamic acid derivatives by iron(III) and manganese(II). *Luminescence*, 2008, 24, 203-208.

Singh et al, Incorporation of siderophore binding sites in a dipodal fluorescent sensor for Fe(III). *Journal of Fluorescence*, 2009, 19(4), 649-654.

Singh et al. A new fluorescent chemosensor for iron(III) based on the β-aminobisulfonate receptor. Tetrahedron Letters, 2009, 50, 953-956.

Staneva et al., A new fluorosensor based on bis-1,8-naphthalimide for metal cations and protons, J. Photochem. Photobiol. A: Chem. 2007, 189, 192-197.

Sun et al.: π-Conjugated poly(anthracene-*alt*-uorene)s with X-shaped repeating units:New blue-light emitting polymers. Polymer, vol. 49, issue 9, Apr. 2008, pp. 2282-2287.

Sung et al., A Fe(3+)/Hg (2+)-selective anthracene-based fluorescent PET sensor with tridentate ionophore of amide/ β-amino alcohol. J Fluoresc, 2007, 17, 383-389.

Tang et al., An unprecedented rhodamine-based fluorescent and colorimetric chemosensor for $Fe^{3+}$ in aqueous media, Monatsh. Chem. 2010, 141, 615-620.

Tasch et al., Red-orange electroluminescence with new soluble and air-stable poly(naphthalene-vinylene)s, Adv. Mater. 1995, 7, 903-906.

Wang et al., Electrospun Nanofibrous Membranes for Highly Sensitive Optical Sensors, Nano Lett. 2002, 2, 1273-1275.

Wang et al., Architecture of a Hybrid Mesoporous Chemosensor for $Fe^{3+}$ by Covalent Coupling Bis-Schiff Base PMBA onto the CPTES-Functionalized SBA-15, J. Phys. Chem. C 2008, 112, 5014-5022.

Wang et al., Selective Detection of Iron(III) by Rhodamine-Modified $Fe_3O_4$ Nanoparticles, Angew. Chem. Int. Ed. 2010, 49, 4576-4579.

Weerasinghe et al., Single- and Multiphoton Turn-On Fluorescent Fe3+ Sensors Based on Bis(rhodamine), J. Phys. Chem. B 2010, 114, 9413-9419.

Wolf et al., Selective detection of Fe(III) ions in aqueous solution with a 1,8-diacridylnaphthalene-derived fluorosensor. *Tetrahedron Letters*, 2004, 45, 7867-7871.

Wu et al., Spiro-Bridged Ladder-Type Poly(p-phenylene)s: Towards Structurally Perfect Light-Emitting Materials, J. Am. Chem. Soc. 2008, 130, 7192-7193.

Xu et al., Cyclodextrin supramolecular complex as a water-soluble ratiometric sensor for ferric ion sensing. *Langmuir*, 2010, 26(6), 4529-4534.

Zhang et al., Novel rare-earth(III)-based water soluble emitters for Fe(III) detection. *Sensors and Actuators, B: Chemical*, 2010, B143(2), 595-599.

Zheng et al., Synthesis and characterization of novel ladder polymer containing diphenylanthracene, Polym. Prepri. 2002, 43(2), 599-600.

Schopov et al., Synthesis and properties of poly(9,10-anthracene diylidene), Polymer, 1978, 19, 1449-1452.

International Search Report and Written Opinion dated Jan. 5, 2012 for PCT Application No. PCT/CN2011/072487, filed Apr. 7, 2011.

Search Report dated Jan. 14, 2015 for Chinese Patent Application No. 2011800698249 filed on Apr. 7, 2011.

POLYANTHRYLENE MATERIALS AND METHODS FOR THEIR PREPARATION AND USE

CROSS-REFERENCE TO RELATED APPLICATIONS

The present application is a divisional under 35 U.S.C. §121 of U.S. patent application Ser. No. 13/505,059, filed Apr. 30, 2012, now U.S. Pat. No. 8,735,166 which is the U.S. National Phase under 35 U.S.C. §371 of International Application No. PCT/CN2011/072487 entitled POLYANTHRYLENE MATERIALS AND METHODS FOR THEIR PREPARATION AND USE, filed Apr. 7, 2011, designating the U.S. All of the aforementioned priority applications are herein expressly incorporated by reference in their entirety.

BACKGROUND

1. Field

The present application relates to compositions and methods for detecting iron in a sample.

2. Description of the Related Art

At present, the common methods used for iron determination include UV-vis spectrophotometry, atomic absorption spectrometry (AAS) and inductively coupled plasma mass spectrometry (ICP-MS). These methods have limited capacity in iron determination because of their inability to detect iron content below ppm level ($10^{-6}$ M), high operation cost, and/or susceptibility to interference from common cations such as Na(I), Ca(II) and Mg(II). In addition, metal ions such as Cu(II) may interfere with detection of iron in chemosensors that utilize low-molecular organic compounds and polymers. There is a need for low-cost iron-sensitive detection methods with anti-interference capabilities.

SUMMARY

Some embodiments disclosed herein include a composition having one or more polyanthrylenes, wherein the one or more polyanthrylenes each independently comprises at least two monomer units represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

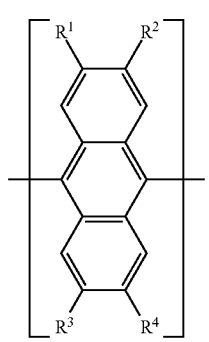

(I)

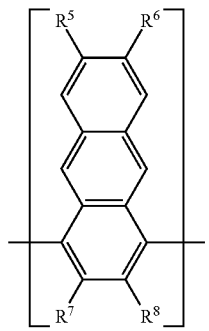

(II)

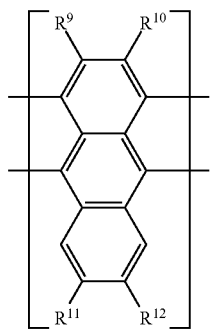

(III)

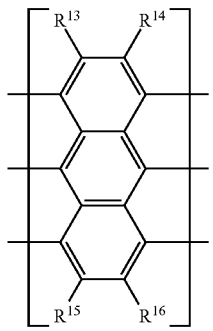

(IV)

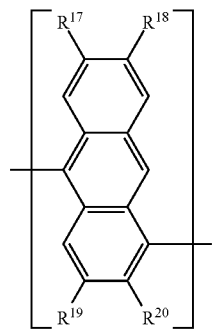

(V)

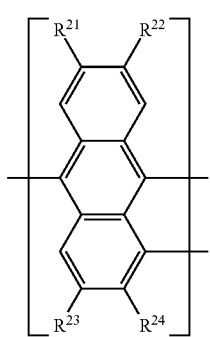
(VI)
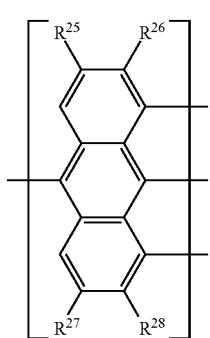
(VII)
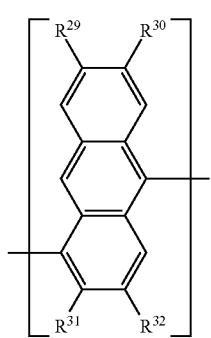
(VIII)
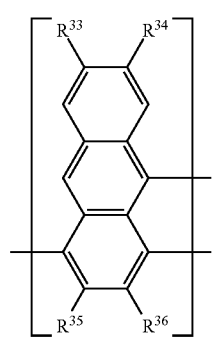
(IX)
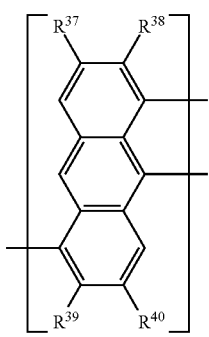
(X)
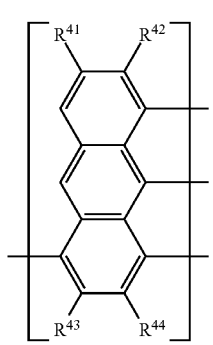
(XI)
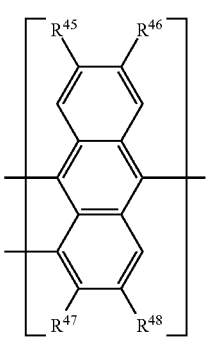
(XII)
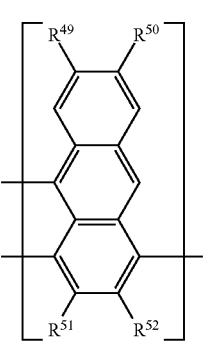
(XIII)

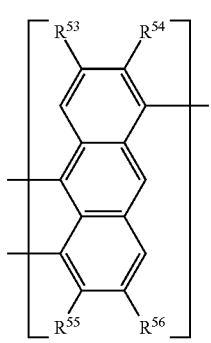
(XIV)

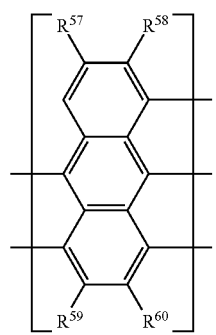
(XV)

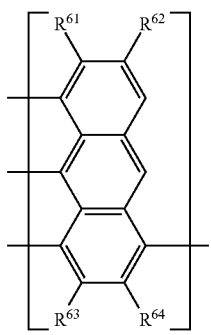
(XVI)

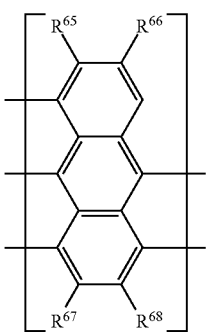
(XVII)

wherein $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen or an electron donating group; and wherein at least one monomer unit in the composition is not represented by Formula I.

In some embodiments, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen. In some embodiments, the electron donating group is selected from the group consisting of $-CH_3$, $-CH_2CH_3$, $-OH$, $-OCH_3$, $-OCH_2CH_3$, $-N(CH_3)_2$, $-N(CH_2CH_3)_2$, and $-SH$.

In some embodiments, at least one of the one or more polyanthrylenes comprises at least three anthracene units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, and Formula XVII, and any combination thereof. In some embodiments, at least one of the one or more polyanthrylenes has a molecular formula selected from the group consisting of $C_{42}H_{22}$, $C_{56}H_{30}$, $C_{70}H_{26}$, $C_{126}H_{68}$, $C_{140}H_{78}$, and $C_{154}H_{84}$. In some embodiments, at least one of the one or more polyanthrylenes has a molecular formula of $C_{42}H_{22}$. In some embodiments, at least one of the one or more polyanthrylenes includes a compound represented by Formula XVIII or Formula XIX:

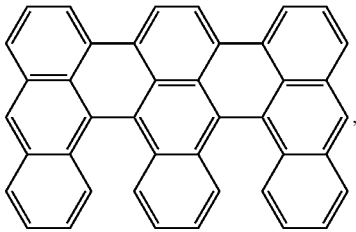
(XVIII)

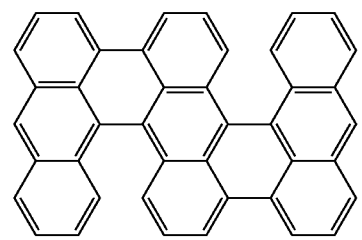
(XIX)

In some embodiments, at least one of the one or more polyanthrylenes has a molecular formula of $C_{56}H_{30}$. In some embodiments, at least one of the one or more polyanthrylenes includes a compound represented by a formula selected from the group consisting of Formula XX, Formula XXI, Formula XXII, and Formula XXIII:

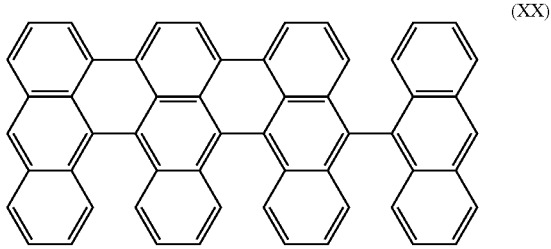 [SMILES: c1ccc2c(-c3c4ccccc4c4c5c3cccc5c3ccc5c6cccc7cc8ccccc8c(c76)c6c7ccccc7c4c3c56)c3ccccc3cc2c1]
(XX)

-continued

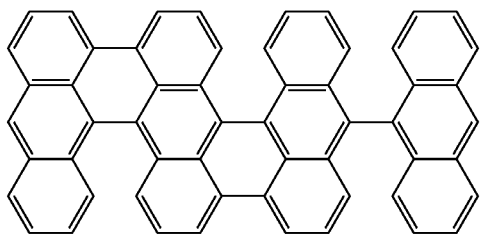
(XXI)

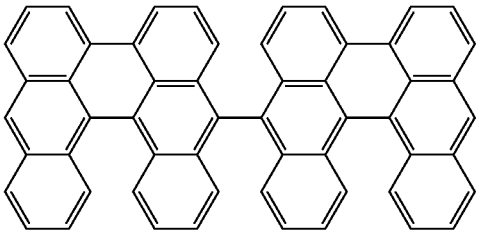
(XXII)

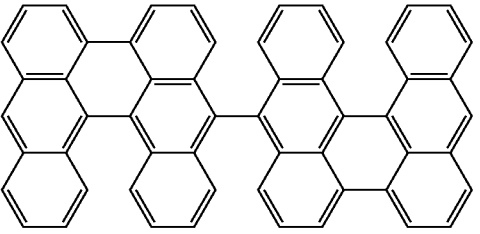
(XXIII)

In some embodiments, at least one of the one or more polyanthrylenes has a molecular formula of $C_{70}H_{26}$. In some embodiments, at least one of the one or more polyanthrylenes has a molecular formula of $C_{126}H_{68}$. In some embodiments, at least one of the one or more polyanthrylenes has a molecular formula of $C_{140}H_{78}$. In some embodiments, at least one of the one or more polyanthrylenes has a molecular formula of $C_{154}H_{84}$. In some embodiments, at least one of the one or more polyanthrylenes includes a compound represented by Formula XXIV:

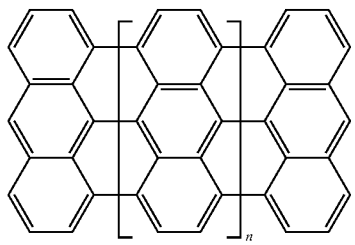
(XXIV)

wherein n is an integer from 1 to 11.

In some embodiments, the composition comprises at least 1 ppm of the one or more polyanthrylenes. In some embodiments, the composition exhibits a peak emission wavelength of about 380 nm to about 650 nm when exposed to ultraviolet or violet radiation. In some embodiments, the average molecular weight of the one or more polyanthrylenes is from about 526 g/mol to about 1932 g/mol. In some embodiments, the average molecular weight of the one or more polyanthrylenes is from about 526 g/mol to about 868 g/mol.

Some embodiments disclosed herein include a method of making a copolymer, the method includes: forming a composition comprising at least one oxidizing agent, at least one co-catalyst and anthracene; and maintaining the composition under conditions effective to covalently bond two or more anthracenes to form one or more polyanthrylenes. In some embodiments, the one or more polyanthrylenes each independently comprises at least two monomer units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

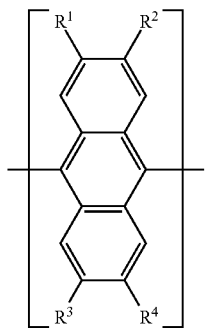
(I)

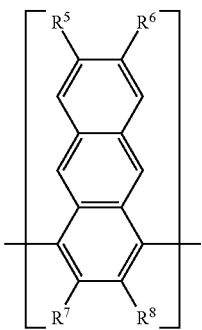
(II)

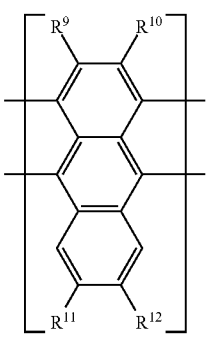
(III)

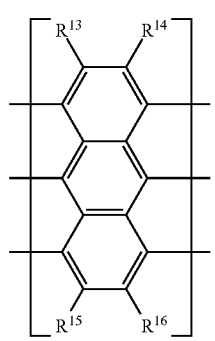 (IV)
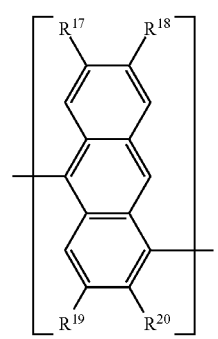 (V)
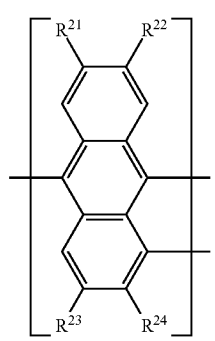 (VI)
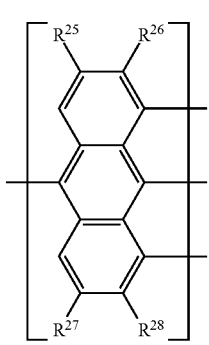 (VII)
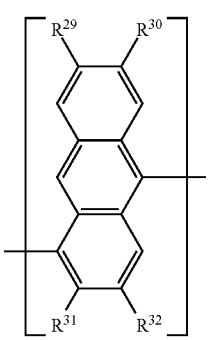 (VIII)
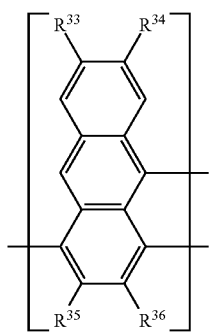 (IX)
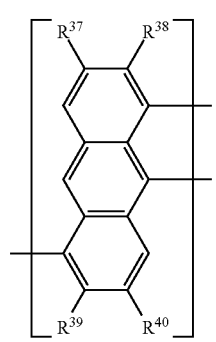 (X)
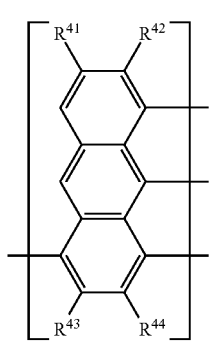 (XI)

-continued

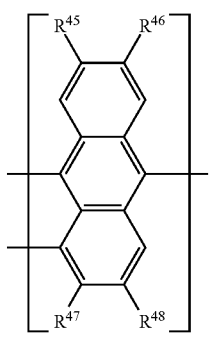
(XII)

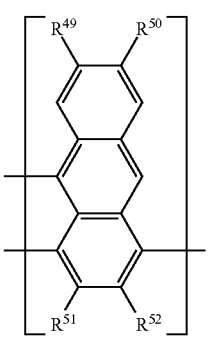
(XIII)

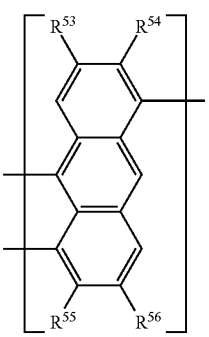
(XIV)

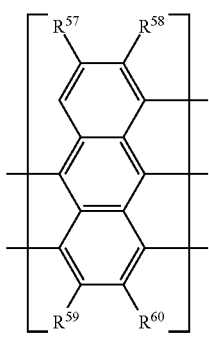
(XV)

-continued

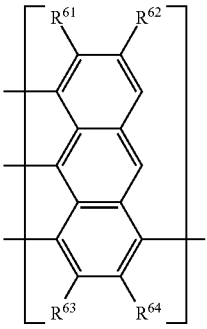
(XVI)

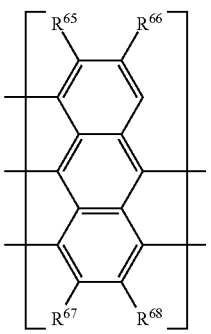
(XVII)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, and $R^{68}$ are each independently hydrogen or an electron donating group; and wherein at least one monomer unit in the composition is not represented by Formula I.

In some embodiments, the molar ratio of the oxidizing agent to anthracene in the composition is less than or equal to about 18:1. In some embodiments, the molar ratio of the oxidizing agent to anthracene in the composition is from about 7:1 to about 9:1. In some embodiments, the oxidizing agent is a Lewis acid. In some embodiments, the Lewis acid is selected from the group consisting of $FeCl_3$, $AlCl_3$—$CuCl_2$, $TiCl_4$, $MoCl_5$, $SbCl_5$, $AsF_5$, and any combination thereof. In some embodiments, the co-catalyst is selected from the group consisting of nitro-alkanes, halogenated alkanes and alkanes. In some embodiments, the co-catalyst is selected from the group consisting of $CH_3NO_2$, $CH_2Cl_2$, n-hexane, $CH_3CH_2NO_2$ and $CH_3CH_2Cl_2$. In some embodiments, the co-catalyst is $CH_3NO_2$, $CH_2Cl_2$ or n-hexane. In some embodiments, the maintaining step is performed at a temperature of about 10° C. to about 80° C. In some embodiments, at least one of the one or more polyanthrylenes has a molecular formula selected from the group consisting of $C_{42}H_{22}$, $C_{56}H_{30}$, $C_{70}H_{26}$, $C_{126}H_{68}$, $C_{140}H_{78}$, and $C_{154}H_{84}$. In some embodiments, at least about 90% by weight of a total amount of aromatic organic compounds in the composition are polyanthrylene.

Some embodiments disclosed herein include an apparatus including: at least one light source configured to emit an ultraviolet or violet radiation, and a composition configured to receive at least a portion of the radiation emitted from the light source, wherein the composition comprises one or more polyanthrylenes, wherein the one or more polyanthrylenes each independently comprises at least two monomer units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

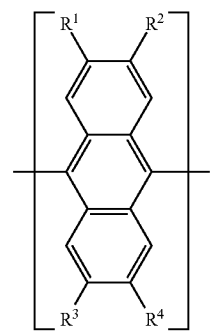
(I)

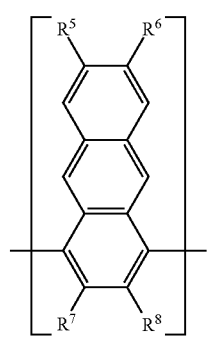
(II)

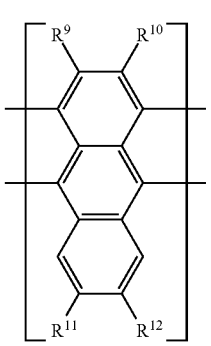
(III)

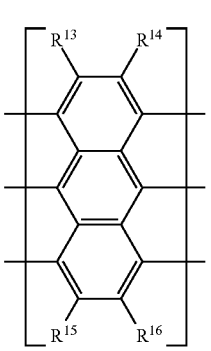
(IV)

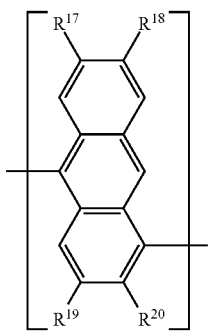
(V)

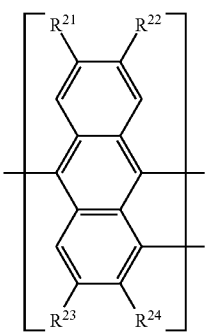
(VI)

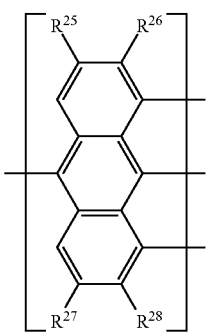
(VII)

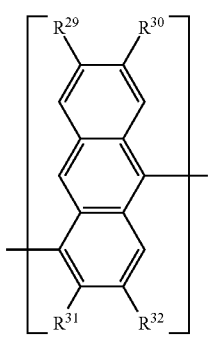
(VIII)

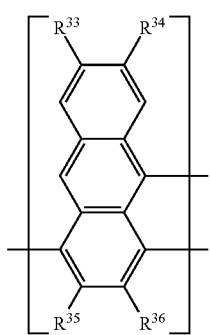 (IX)
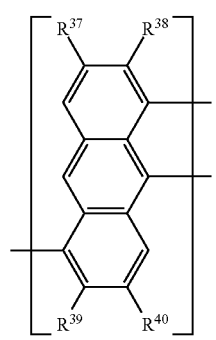 (X)
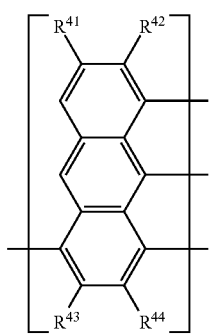 (XI)
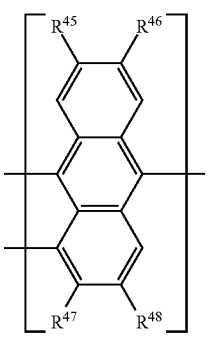 (XII)
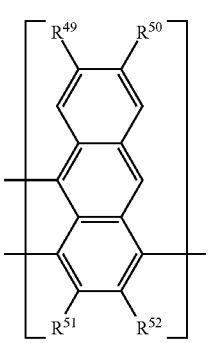 (XIII)
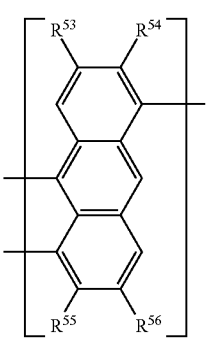 (XIV)
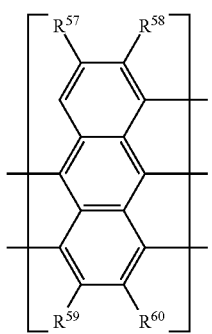 (XV)
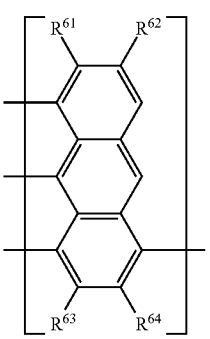 (XVI)

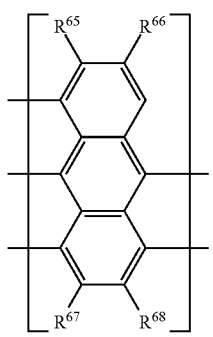

(XVII)

wherein $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen or an electron donating group; and wherein at least one monomer unit in the composition is not represented by Formula I.

In some embodiments, the apparatus further comprises at least one light detector configured to measure light emitted from the composition. In some embodiments, the apparatus further comprises a housing, wherein the housing contains the composition and is configured to receive a sample adjacent to the composition.

Some embodiments disclosed herein include a method for detecting ferric ions from a sample, the method includes: providing a sample suspected of containing one or more ferric ions; and contacting the sample with a composition to form a mixture, wherein the composition comprises one or more polyanthrylenes, wherein the one or more polyanthrylenes each independently comprises at least two monomer units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

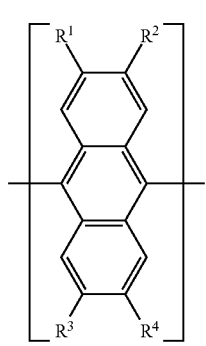

(I)

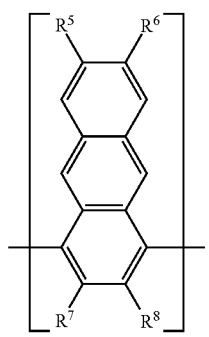

(II)

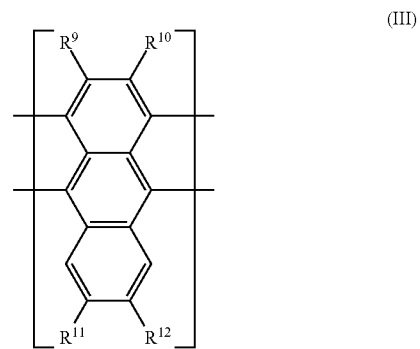

(III)

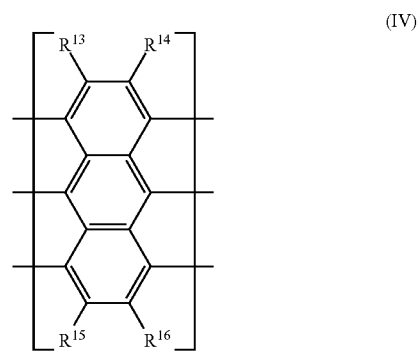

(IV)

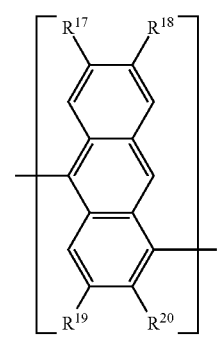

(V)

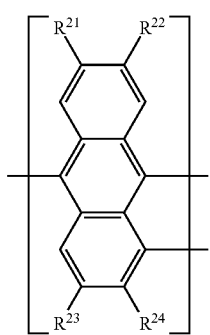
(VI)
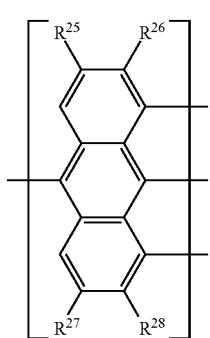
(VII)
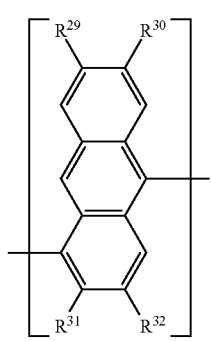
(VIII)
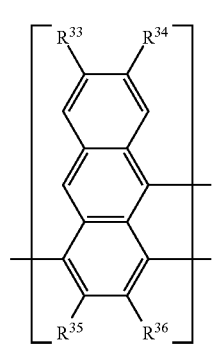
(IX)
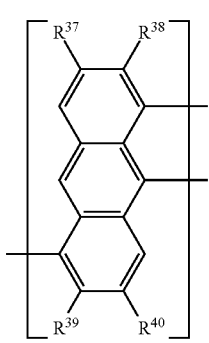
(X)
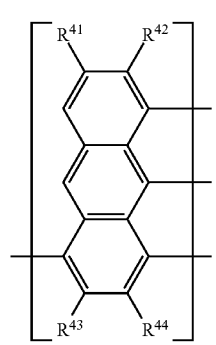
(XI)
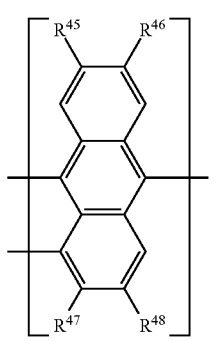
(XII)
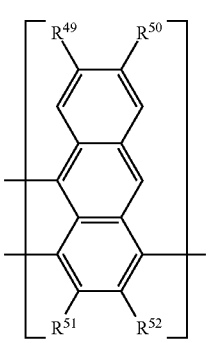
(XIII)

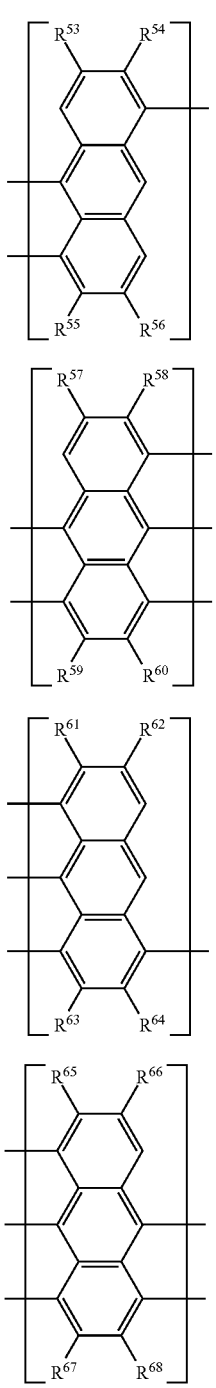

(XIV)

(XV)

(XVI)

(XVII)

wherein $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen or an electron donating group, and wherein at least one monomer unit in the composition is not represented by Formula I;

exposing the mixture to a radiation effective to produce fluorescence from the composition; and measuring the amount of fluorescence produced by the mixture In some embodiments, the produced fluorescence is greater in the absence of ferric ions than in the presence of ferric ions. In some embodiments, the concentration of the ferric ions in the sample is from about $10^{-3}$ M to about $10^{-9}$ M. In some embodiments, the concentration of the ferric ions in the sample is from about $10^{-6}$ M to about $10^{-9}$ M.

BRIEF DESCRIPTION OF THE DRAWINGS

FIG. 6a shows the 400 MHz $^1H$-$^1H$ COSY spectra of An; FIG. 6b shows the 400 MHz $^1H$-$^1H$ COSY spectra of soluble part of the PAn; FIG. 6c shows 500 MHz $^1H$-NMR spectra of An and soluble part of the PAn in DMSO-d6. The arrows in FIG. 6c represent the correlation of two types of adjacent hydrogen protons.

DETAILED DESCRIPTION

Figure 1:
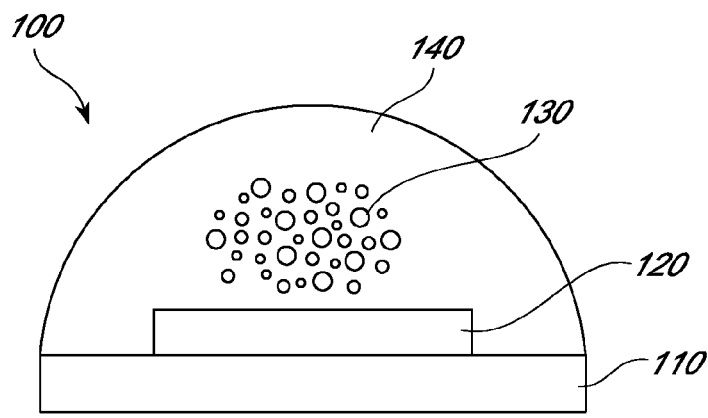
FIG. 1 depicts an illustrative embodiment of a lighting apparatus that is within the scope of the present application (not to scale).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Disclosed herein are compounds including one or more polyanthrylene. These compounds may, for example, exhibit superior fluorescence properties. The compounds may also provide, in some embodiments, highly sensitive detection of iron, such as ferric ions. The present application also relates to methods of making these compounds, method of using these compounds, and apparatuses that include these compounds.

Definitions

As used herein, the term "electron donating" refers to the ability of a substituent to donate electrons relative to that of hydrogen if the hydrogen atom occupied the same position in the molecule. This term is well understood by one skilled in the art and discussed in Advanced Organic Chemistry by M. Smith and J. March, John Wiley and Sons, New York N.Y. (2007). Non-limiting examples of electron donating group include —$CH_3$, —$CH_2CH_3$, —OH, —$OCH_3$, —$OCH_2CH_3$, —$N(CH_3)_2$, —$N(CH_2CH_3)_2$, and —SH.

Compositions Including Polyanthrylene

Some embodiments disclosed herein include a composition having one or more polyanthrylenes, wherein the one or more polyanthrylenes each independently comprises at least two monomer units represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

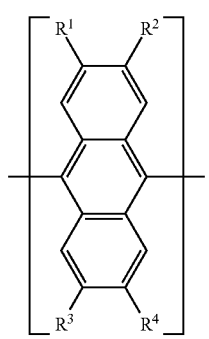

(I)

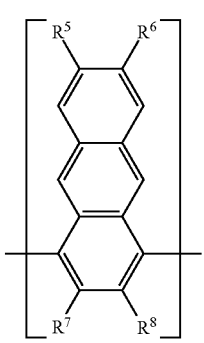

(II)

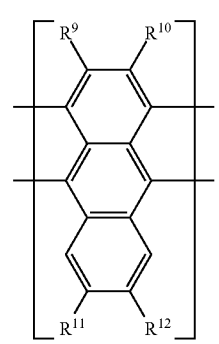

(III)

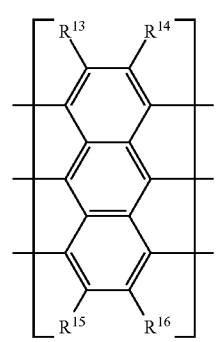

(IV)

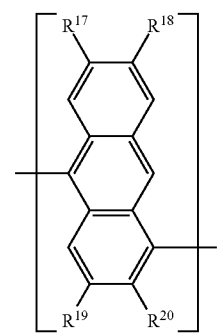

(V)

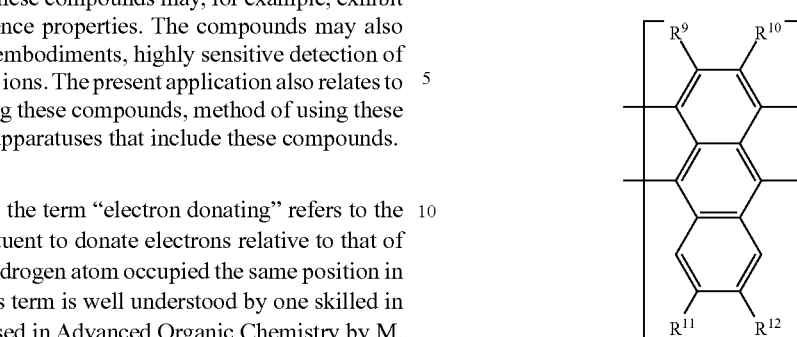

(VI)

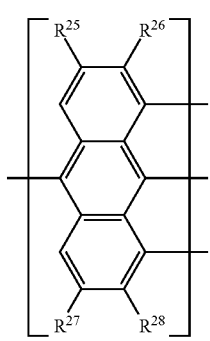 (VII)
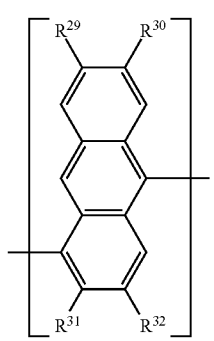 (VIII)
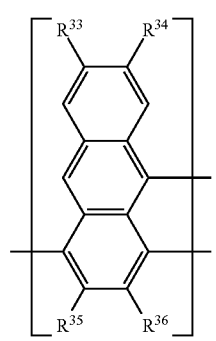 (IX)
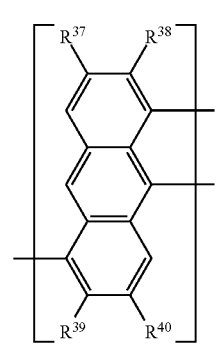 (X)
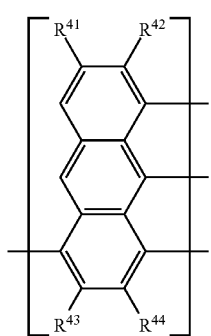 (XI)
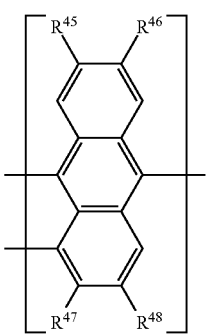 (XII)
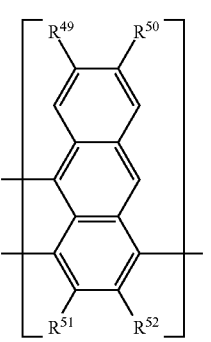 (XIII)
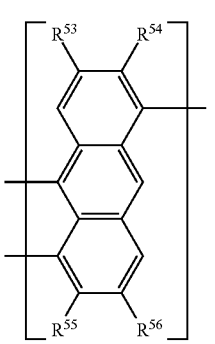 (XIV)

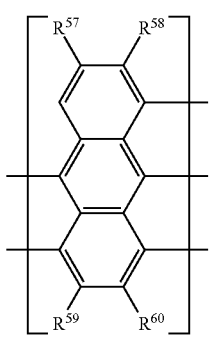

(XV)

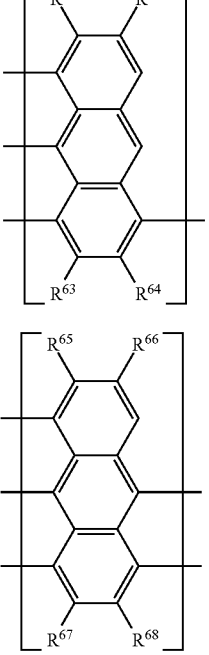

(XVI)

(XVII)

wherein $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen or an electron donating group; and wherein at least one monomer unit in the composition is not represented by Formula I.

In some embodiments, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$ and $R^{68}$ are hydrogen.

Examples of electron donating group include, but are not limited, to —CH$_3$, —CH$_2$CH$_3$, —OH, —OCH$_3$, —OCH$_2$CH$_3$, —N(CH$_3$)$_2$, —N(CH$_2$CH$_3$)$_2$, and —SH. In some embodiments, the electron donating group does not include —NH$_2$, —NHCH$_3$ and —NHCH$_2$CH$_3$.

For purposes of the present application, the nomenclature for anthracene units with the polyanthrylene is shown below:

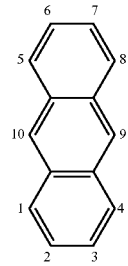

As noted above, the polyanthrylene can include two or more anthracene units. The two anthracene units can be linked together to form the polyanthrylene. In some embodiments, the polyanthrylene includes at least two anthracene units that are covalently bonded together by one or more carbon-carbon bonds. For example, a polyanthrylene can include two anthracene units with a covalent bond between the 5- and the 8-positions, the 10- and the 9-positions, or the 1- and the 4-positions on the respective anthracene unit.

In some embodiments, at least a portion of the anthracene units (e.g., two, three, four, five, six, seven, eight, nine, ten or more anthracene units) in the polyanthrylene each have one, two, or more carbon-carbon bonds linking with one or more anthracene units. In some embodiments, all of the anthracene units in the polyanthrylene each include, one, two, or more carbon-carbon bonds linking with at least one other anthracene unit. As one example, the polyanthrylene represented by Formula XVIII includes one anthracene unit that include carbon-carbon bonds at the 8- and 9-positions which link to one other anthracene unit, one anthracene unit that includes carbon-carbon bonds at the 5-, 10-, 8- and 9-positions which link to two other anthracene units, and one anthracene unit that includes carbon-carbon bonds at the 5- and 10-positions which link to one other anthracene unit.

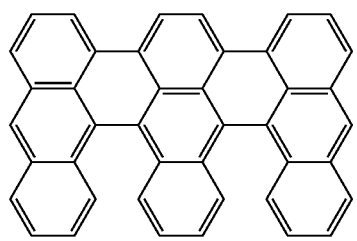 [SMILES: c1ccc2c(c1)cc1cccc3c4ccc5c6cccc7cc8ccccc8c(c76)c6c7ccccc7c(c2c13)c4c56]

(XVIII)

As another example, the polyanthrylene represented by Formula XIX includes one anthracene unit that include carbon-carbon bonds at the 8- and 9-positions which link to one other anthracene unit, one anthracene unit that includes carbon-carbon bonds at the 5-, 10-, 9- and 4-positions which link to two other anthracene units, and one anthracene unit that includes carbon-carbon bonds at the 10- and 1-positions which link to one other anthracene unit.

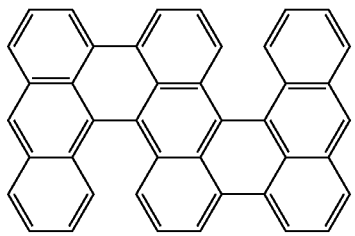

(XIX)

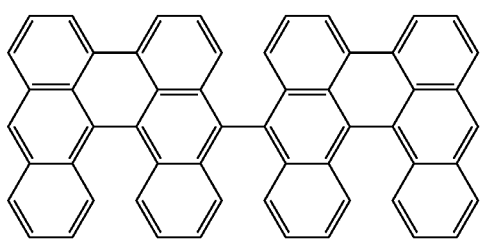

(XXII)

As still another example, the polyanthrylene represented by Formula XX includes one anthracene unit that includes carbon-carbon bonds at the 8- and 9-positions which link to one other anthracene unit, one anthracene unit that includes carbon-carbon bonds at the 5-, 10-, 8- and 9-positions which link to two other anthracene units, one anthracene unit that includes carbon-carbon bonds at the 5-, 10- and 9-positions which link to two other anthracene units, and one anthracene unit that includes a carbon-carbon bond at the 10-position which links to one other anthracene unit.

As another example, the polyanthrylene represented by Formula XXIII includes one anthracene unit that includes carbon-carbon bonds at the 8- and 9-positions which link to one other anthracene unit, one anthracene unit that includes carbon-carbon bonds at the 5-, 10- and 9-positions which link to two other anthracene units, one anthracene unit that includes carbon-carbon bonds at the 10-, 9- and 4-positions which link to two other anthracene units, and one anthracene unit that includes carbon-carbon bonds at the 10- and 1-position which links to one other anthracene unit.

(XX)

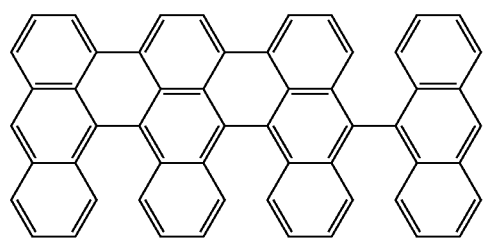 [SMILES: c1ccc2c(-c3c4ccccc4c4c5c3cccc5c3ccc5c6cccc7cc8ccccc8c(c76)c6c7ccccc7c4c3c56)c3ccccc3cc2c1]

(XXIII)

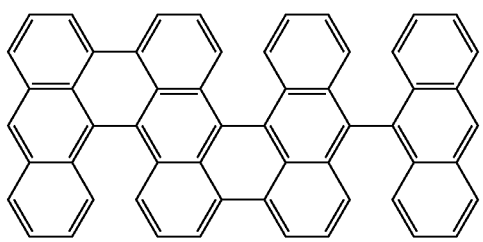

As yet another example, the polyanthrylene represented by Formula XXI includes one anthracene unit that includes carbon-carbon bonds at the 8- and 9-positions which link to one other anthracene unit, one anthracene unit that includes carbon-carbon bonds at the 5-, 10-, 9- and 4-positions which link to two other anthracene units, one anthracene unit that includes carbon-carbon bonds at the 10-, 1- and 9-positions which link to two other anthracene units, and one anthracene unit that includes a carbon-carbon bond at the 10-position which links to one other anthracene unit.

(XXI)

As yet still another example, the polyanthrylene represented by Formula XXII includes one anthracene unit that includes carbon-carbon bonds at the 8- and 9-positions which link to one other anthracene unit, one anthracene unit that includes carbon-carbon bonds at the 5-, 10- and 9-positions which link to two other anthracene units, one anthracene unit that includes carbon-carbon bonds at the 10-, 8- and 9-positions which link to two other anthracene units, and one anthracene unit that includes carbon-carbon bonds at the 5- and 10-position which links to one other anthracene unit.

In some embodiments, at least a portion of the anthracene units (e.g., one, two, three, four, five, six, seven, or more of the anthracene units) in the polyanthrylene each include one or two carbon-carbon bonds linking with one or two other anthracene units. In some embodiments, all of the anthracene units in the polyanthrylene each include one or two carbon-carbon bonds linking with one or two other anthracene units. In some embodiments, at least a portion of the anthracene units in the polyanthrylene each include two carbon-carbon bonds linking with one or two other anthracene units. In some embodiments, at least a portion of the anthracene units in the polyanthrylene each include three carbon-carbon bonds linking with one or two other anthracene units. In some embodiments, at least a portion of the anthracene units in the polyanthrylene each include four, five or six carbon-carbon bonds linking with two other anthracene units.

In some embodiments, at least a portion of the anthracene units (e.g., one, two, three, four, five, six, seven, or more of the anthracene units) in the polyanthrylene each include two or more carbon-carbon bonds linking with one, two, or more other anthracene units, where each carbon-carbon bond is attached on each anthracene unit at a carbon position independently selected from 1, 4, 5, 8, 9, and 10.

In some embodiments, at least a portion of the anthracene units (e.g., one, two, three, four, five, six, seven, or more of the anthracene units) in the polyanthrylene each include two carbon-carbon bonds linking with two other anthracene units, where each carbon-carbon bond is attached on each anthracene unit at a carbon position independently selected from 10 and 9. As one example, the polyanthrylene can include one or more anthracene units represented by Formula I:

(I)

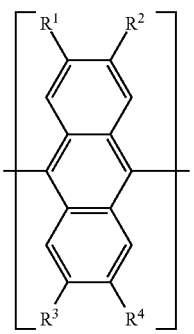

In some embodiments, at least a portion of the anthracene units (e.g., one, two, three, four, five, six, seven, or more of the anthracene units) in the polyanthrylene each include two carbon-carbon bonds linking with two other anthracene units, where each carbon-carbon bond is attached on each anthracene unit at a carbon position independently selected from 1 and 4. As one example, the polyanthrylene can include one or more anthracene units represented by Formula II:

(II)

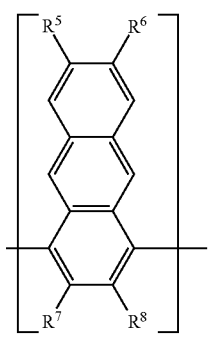

In some embodiments, at least a portion of the anthracene units (e.g., one, two, three, four, five, six, seven, or more of the anthracene units) in the polyanthrylene each include four carbon-carbon bonds linking with two other anthracene units, where each carbon-carbon bond is attached on each anthracene unit at a carbon position independently selected from 5, 8, 10, and 9. As one example, the polyanthrylene can include one or more anthracene units represented by Formula III:

(III)

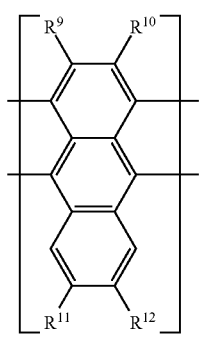

In some embodiments, at least a portion of the anthracene units (e.g., one, two, three, four, five, six, seven, or more of the anthracene units) in the polyanthrylene each include six carbon-carbon bonds linking with two other anthracene units, where each carbon-carbon bond is attached on each anthracene unit at a carbon position independently selected from 5, 8, 10, 9, 1, and 4. As one example, the polyanthrylene can include one or more anthracene units represented by Formula IV:

(IV)

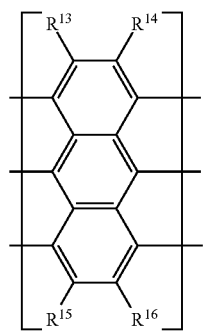

In some embodiments, at least a portion of the anthracene units (e.g., one, two, three, four, five, six, seven, or more of the anthracene units) in the polyanthrylene each include two carbon-carbon bonds linking with two other anthracene units, where each carbon-carbon bond is attached on each anthracene unit at a carbon position independently selected from 10 and 4. As one example, the polyanthrylene can include one or more anthracene units represented by Formula V:

(V)

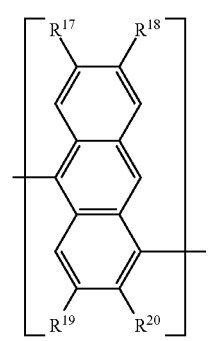

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 10, 9 and 4. As one example, the polyanthrylene can include one or more anthracene units represented by Formula VI:

(VI)

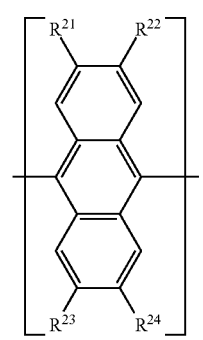

In some embodiments, at least a portion of the anthracene units (e.g., one, two, three, four, five, six, seven, or more of the anthracene units) in the polyanthrylene each include four carbon-carbon bonds linking with two other anthracene units, where each carbon-carbon bond is attached on each anthracene unit at a carbon position independently selected from 10, 8, 9 and 4. As one example, the polyanthrylene can include one or more anthracene units represented by Formula VII:

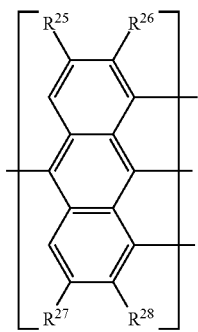

(VII)

In some embodiments, at least a portion of the anthracene units (e.g., one, two, three, four, five, six, seven, or more of the anthracene units) in the polyanthrylene each include two carbon-carbon bonds linking with two other anthracene units, where each carbon-carbon bond is attached on each anthracene unit at a carbon position independently selected from 1 and 9. As one example, the polyanthrylene can include one or more anthracene units represented by Formula VIII:

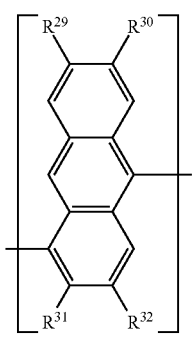

(VIII)

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 1, 9 and 4. As one example, the polyanthrylene can include one or more anthracene units represented by Formula IX:

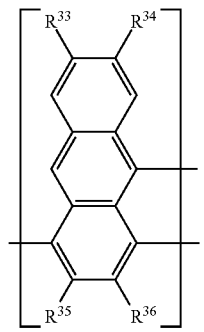

(IX)

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 1, 8 and 9. As one example, the polyanthrylene can include one or more anthracene units represented by Formula X:

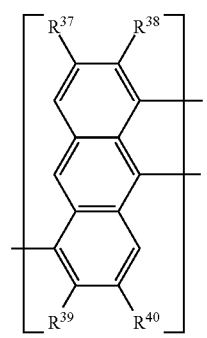

(X)

In some embodiments, at least a portion of the anthracene units (e.g., one, two, three, four, five, six, seven, or more of the anthracene units) in the polyanthrylene each include four carbon-carbon bonds linking with two other anthracene units, where each carbon-carbon bond is attached on each anthracene unit at a carbon position independently selected from 1, 8, 9, and 4. As one example, the polyanthrylene can include one or more anthracene units represented by Formula XI:

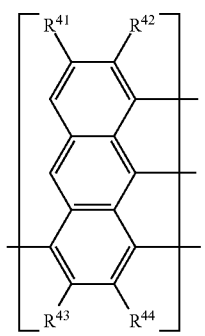

(XI)

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 10, 1 and 9. As one example, the polyanthrylene can include one or more anthracene units represented by Formula XII:

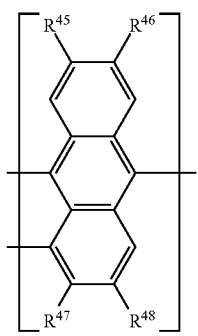

(XII)

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 10, 1 and 4. As one example, the polyanthrylene can include one or more anthracene units represented by Formula XIII:

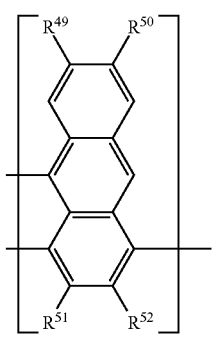

(XIII)

In some embodiments, at least a portion of the anthracene units (e.g., one, two, three, four, five, six, seven, or more of the anthracene units) in the polyanthrylene each include three carbon-carbon bonds linking with two other anthracene units, where each carbon-carbon bond is attached on each anthracene unit at a carbon position independently selected from 10, 1 and 8. As one example, the polyanthrylene can include one or more anthracene units represented by Formula XIV:

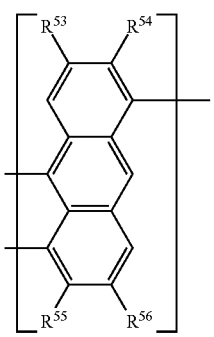

(XIV)

In some embodiments, at least a portion of the anthracene units (e.g., one, two, three, four, five, six, seven, or more of the anthracene units) in the polyanthrylene each include five carbon-carbon bonds linking with two other anthracene units, where each carbon-carbon bond is attached on each anthracene unit at a carbon position independently selected from 10, 1, 8, 9 and 4. As one example, the polyanthrylene can include one or more anthracene units represented by Formula XV:

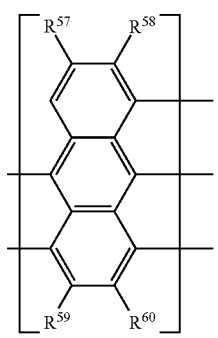

(XV)

In some embodiments, at least a portion of the anthracene units (e.g., one, two, three, four, five, six, seven, or more of the anthracene units) in the polyanthrylene each include four carbon-carbon bonds linking with two other anthracene units, where each carbon-carbon bond is attached on each anthracene unit at a carbon position independently selected from 5, 10, 1, and 4. As one example, the polyanthrylene can include one or more anthracene units represented by Formula XVI:

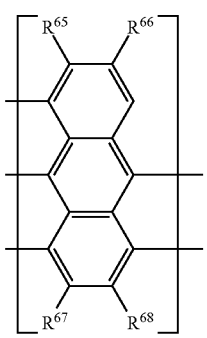

(XVII)

In some embodiments, at least a portion of the anthracene units (e.g., one, two, three, four, five, six, seven, or more of the anthracene units) in the polyanthrylene each include five carbon-carbon bonds linking with two other anthracene units, where each carbon-carbon bond is attached on each anthracene unit at a carbon position independently selected from 5, 10, 1, 9, and 4. As one example, the polyanthrylene can include one or more anthracene units represented by Formula XVII:

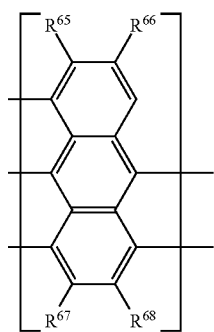

(XVII)

The one or more polyanthrylenes in the composition can, in some embodiments, be selected from compounds represented by the chemical formula $C_{14m}H_{10m-2x}$, where m is an integer greater than one (e.g., 2, 3, 4, 5, or more), and x is an integer that is greater than or equal to (m−1) and is less than or equal to 3(m−1) (i.e., m−1≤x≤3(m−1)). In some embodiments, m can be 2, 3, 4, 5, 6, 7, 8, 9, 10, 11, 12, 13, 14, or 15. In some embodiments, m can be 3, 4, 5, 6, 7, 8, 9, 10, or 11. In some embodiments, m can be 3, 4 or 5. Non-limiting examples of chemical formulas that can represent one or more polyanthrylenes in the composition include $C_{28}H_{16}$, $C_{28}H_{14}$, $C_{42}H_{24}$, $C_{42}H_{22}$, $C_{42}H_{20}$, $C_{42}H_{18}$, $C_{56}H_{32}$, $C_{56}H_{30}$, $C_{56}H_{28}$, $C_{56}H_{26}$, $C_{56}H_{24}$, $C_{56}H_{22}$, $C_{70}H_{40}$, $C_{70}H_{38}$, $C_{70}H_{36}$, $C_{70}H_{34}$, $C_{70}H_{32}$, $C_{70}H_{30}$, $C_{70}H_{28}$, $C_{70}H_{26}$, $C_{84}H_{48}$, $C_{84}H_{46}$, $C_{84}H_{44}$, $C_{84}H_{42}$, $C_{84}H_{40}$, $C_{84}H_{38}$, $C_{84}H_{36}$, $C_{84}H_{34}$, $C_{84}H_{32}$, $C_{84}H_{30}$, $C_{98}H_{56}$, $C_{98}H_{54}$, $C_{98}H_{52}$, $C_{98}H_{50}$, $C_{98}H_{48}$, $C_{98}H_{46}$, $C_{98}H_{44}$, $C_{98}H_{42}$, $C_{98}H_{40}$, $C_{98}H_{38}$, $C_{98}H_{36}$, $C_{98}H_{34}$, $C_{112}H_{64}$, $C_{112}H_{62}$, $C_{112}H_{60}$, $C_{112}H_{58}$, $C_{112}H_{56}$, $C_{112}H_{54}$, $C_{112}H_{52}$, $C_{112}H_{50}$, $C_{112}H_{48}$, $C_{112}H_{46}$, $C_{112}H_{44}$, $C_{112}H_{42}$, $C_{112}H_{40}$, $C_{112}H_{38}$, $C_{126}H_{72}$, $C_{126}H_{70}$, $C_{126}H_{68}$, $C_{126}H_{66}$, $C_{126}H_{64}$, $C_{126}H_{62}$, $C_{126}H_{60}$, $C_{126}H_{58}$, $C_{126}H_{56}$, $C_{126}H_{54}$, $C_{126}H_{52}$, $C_{126}H_{50}$, $C_{126}H_{48}$, $C_{126}H_{46}$, $C_{126}H_{44}$, $C_{126}H_{42}$, $C_{140}H_{80}$, $C_{140}H_{78}$, $C_{140}H_{76}$, $C_{140}H_{74}$, $C_{140}H_{72}$, $C_{140}H_{70}$, $C_{140}H_{68}$, $C_{140}H_{66}$, $C_{140}H_{64}$, $C_{140}H_{62}$, $C_{140}H_{60}$, $C_{140}H_{58}$, $C_{140}H_{56}$, $C_{140}H_{54}$, $C_{140}H_{52}$, $C_{140}H_{50}$, $C_{140}H_{48}$, $C_{140}H_{46}$, $C_{154}H_{88}$, $C_{154}H_{86}$, $C_{154}H_{84}$, $C_{154}H_{82}$, $C_{154}H_{80}$, $C_{154}H_{78}$, $C_{154}H_{76}$, $C_{154}H_{74}$, $C_{154}H_{72}$, $C_{154}H_{70}$, $C_{154}H_{68}$, $C_{154}H_{66}$, $C_{154}H_{64}$, $C_{154}H_{62}$, $C_{154}H_{60}$, $C_{154}H_{58}$, $C_{154}H_{56}$, $C_{154}H_{54}$, $C_{154}H_{52}$ and $C_{154}H_{50}$. In some embodiments, one or more polyanthrylenes in the composition can be represented by chemical formulas such as $C_{42}H_{22}$, $C_{56}H_{30}$, $C_{70}H_{26}$, $C_{126}H_{68}$, $C_{140}H_{78}$, and $C_{154}H_{84}$. In some embodiments, one or more polyanthrylenes in the composition can be represented by chemical formula XXIV, where n is an integer from 1 to 11.

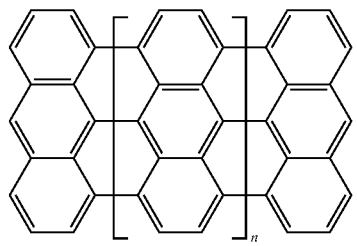

(XXIV)

The total amount of anthracene units in each polyanthrylene can vary. Each polyanthrylene can include, for example, two, three, four, five, six, seven, or more anthracene units. In some embodiments, only anthracene units are incorporated into the polyanthrylene. That is, no other monomer units, such as pyrrole, are linked (e.g., covalently bonded) with the anthracene units in the polyanthrylene. In some embodiments, the polyanthrylene consists of anthracene units.

The total amount of the one or more polyanthrylenes in the composition is not particularly limited and can vary depending upon the desired use. For example, a relatively small amount of one or more polyanthrylenes can be used for certain applications to detect iron ions that are discussed further below. The total amount of the one or more polyanthrylenes may, for example, be at least about 1 ppm; at least about 10 ppm; at least about 20 ppm; at least about 50 ppm; at least about 1% by weight; at least about 2% by weight; or at least about 5% by weight. The total amount of the one or more polyanthrylenes in the composition may, for example, be less than or equal to about 100% by weight, less than or equal to about 99% by weight; less than or equal to about 90% by weight; less than or equal to about 70% by weight; less than or equal to about 50% by weight; less than or equal to about 30% by weight; less than or equal to about 10% by weight; less than or equal to about 1% by weight; less than or equal to about 500 ppm. In some embodiments, the total amount of the one or more polyanthrylene in the composition is about 20 ppm.

In some embodiments, the average molecular weight of the one or more polyanthrylenes is from about 526 g/mol to about 1932 g/mol. In some embodiments, the average molecular weight of the one or more polyanthrylenes is from about 526 g/mol to about 868 g/mol.

It will be appreciated that the "total amount" of the one or more polyanthrylenes can include the combined amount of two or more different polyanthrylene compounds. For example, the total amount of the one or more polyanthrylenes can be the combined amount of polyanthrylenes represented by the chemical formulas $C_{42}H_{22}$ and $C_{56}H_{30}$. The total amount of the one or more polyanthrylenes can also be expressly limited to one or more specific compounds (or a sub-genus of compounds) disclosed in the present application.

In some embodiments, the one or more polyanthrylenes that can be in the composition include a compound represented by Formula XVIII, a compound represented by Formula XIX, a compound represented by Formula XX, a compound of Formula XXI, a compound of Formula XXII, a compound of Formula XXIII, a compound of Formula XXV, a compound of Formula XXVI, a compound of Formula XXVII, and a compound of Formula XXVIII:

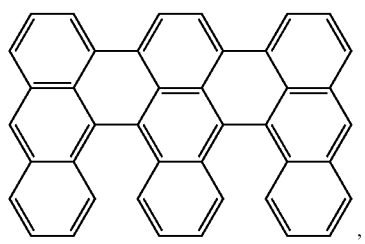
(XVIII)
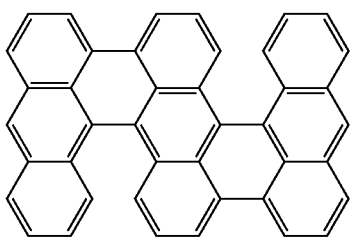
(XIX)
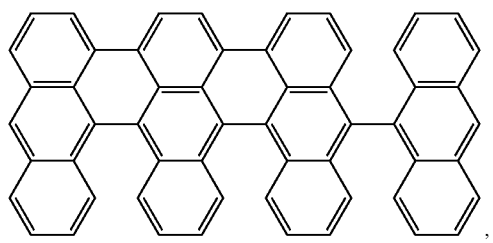
(XX)
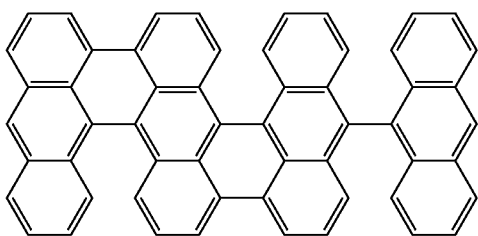
(XXI)
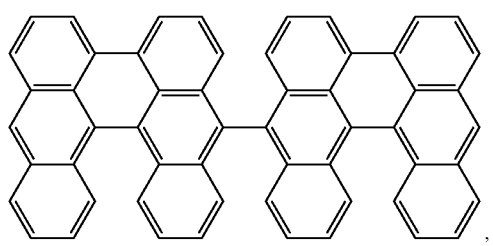
(XXII)
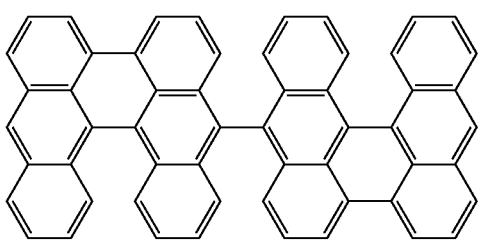
(XXIII)
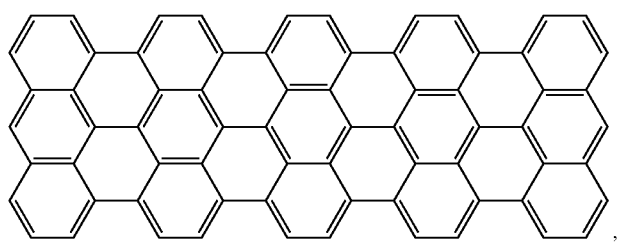
(XXV)
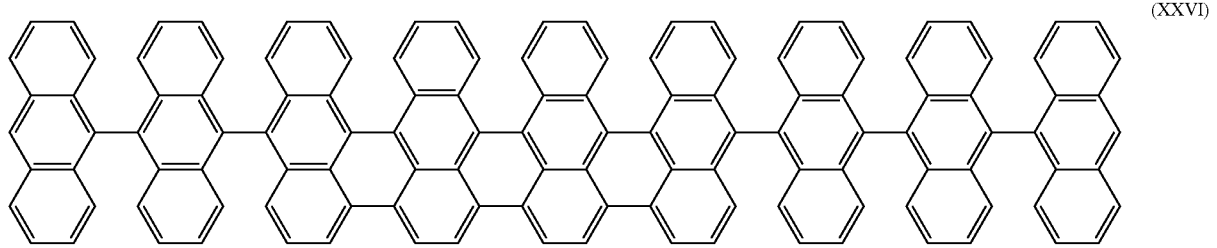
(XXVI)
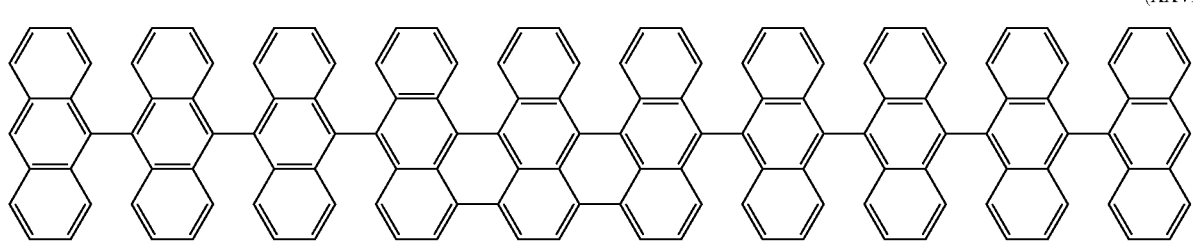
(XXVII)

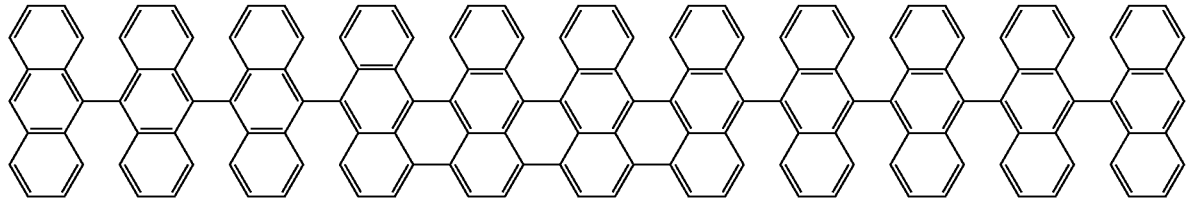
(XXVIII)

The composition can also include, in some embodiments, two or more (e.g., two, three, four, or more) polyanthrylenes. The two or more polyanthrylenes can be any of those disclosed in the present application. For example, the composition can include a compound represented by Formula XX and a compound represented by Formula XXI. In some embodiments, the composition includes two or more (e.g., two, three, four, or more) polyanthrylenes that are each compounds represented by different chemical formulas. The chemical formulas can be, for example, two or more selected from $C_{28}H_{16}$, $C_{28}H_{14}$, $C_{42}H_{24}$, $C_{42}H_{22}$, $C_{42}H_{20}$, $C_{42}H_{18}$, $C_{56}H_{32}$, $C_{56}H_{30}$, $C_{56}H_{28}$, $C_{56}H_{26}$, $C_{56}H_{24}$, $C_{56}H_{22}$, $C_{70}H_{40}$, $C_{70}H_{38}$, $C_{70}H_{36}$, $C_{70}H_{34}$, $C_{70}H_{32}$, $C_{70}H_{30}$, $C_{70}H_{28}$, $C_{70}H_{26}$, $C_{84}H_{48}$, $C_{84}H_{46}$, $C_{84}H_{44}$, $C_{84}H_{42}$, $C_{84}H_{40}$, $C_{84}H_{38}$, $C_{84}H_{36}$, $C_{84}H_{34}$, $C_{84}H_{32}$, $C_{84}H_{30}$, $C_{98}H_{56}$, $C_{98}H_{54}$, $C_{98}H_{52}$, $C_{98}H_{50}$, $C_{98}H_{48}$, $C_{98}H_{46}$, $C_{98}H_{44}$, $C_{98}H_{42}$, $C_{98}H_{40}$, $C_{98}H_{38}$, $C_{98}H_{36}$, $C_{98}H_{34}$, $C_{112}H_{64}$, $C_{112}H_{62}$, $C_{112}H_{60}$, $C_{112}H_{58}$, $C_{112}H_{56}$, $C_{112}H_{54}$, $C_{112}H_{52}$, $C_{112}H_{50}$, $C_{112}H_{48}$, $C_{112}H_{46}$, $C_{112}H_{44}$, $C_{112}H_{42}$, $C_{112}H_{40}$, $C_{112}H_{38}$, $C_{126}H_{72}$, $C_{126}H_{70}$, $C_{126}H_{68}$, $C_{126}H_{66}$, $C_{126}H_{64}$, $C_{126}H_{62}$, $C_{126}H_{60}$, $C_{126}H_{58}$, $C_{126}H_{56}$, $C_{126}H_{54}$, $C_{126}H_{52}$, $C_{126}H_{50}$, $C_{126}H_{48}$, $C_{126}H_{46}$, $C_{126}H_{44}$, $C_{126}H_{42}$, $C_{140}H_{80}$, $C_{140}H_{78}$, $C_{140}H_{76}$, $C_{140}H_{74}$, $C_{140}H_{72}$, $C_{140}H_{70}$, $C_{140}H_{68}$, $C_{140}H_{66}$, $C_{140}H_{64}$, $C_{140}H_{62}$, $C_{140}H_{60}$, $C_{140}H_{58}$, $C_{140}H_{56}$, $C_{140}H_{54}$, $C_{140}H_{52}$, $C_{140}H_{50}$, $C_{140}H_{48}$, $C_{140}H_{46}$, $C_{154}H_{88}$, $C_{154}H_{86}$, $C_{154}H_{84}$, $C_{154}H_{82}$, $C_{154}H_{80}$, $C_{154}H_{78}$, $C_{154}H_{76}$, $C_{154}H_{74}$, $C_{154}H_{72}$, $C_{154}H_{70}$, $C_{154}H_{68}$, $C_{154}H_{66}$, $C_{154}H_{64}$, $C_{154}H_{62}$, $C_{154}H_{60}$, $C_{154}H_{58}$, $C_{154}H_{56}$, $C_{154}H_{54}$, $C_{154}H_{52}$ and $C_{154}H_{50}$. In some embodiments, the composition includes two or more (e.g., two, three, four, or more) polyanthrylenes that are each different compounds selected from a compound represented by Formula XVIII, a compound represented by Formula XIX, a compound represented by Formula XX, a compound of Formula XXI, a compound of Formula XXII, a compound of Formula XXIII, a compound of Formula XXV, a compound of Formula XXVI, a compound of Formula XXVII, and a compound of Formula XXVIII.

The composition can be in the form of a liquid that includes the one or more polyanthrylenes. For example, the one or more polyanthrylenes can be dispersed or dissolved in a solvent. The solvent can be an organic solvent or water. The organic solvent may, for example, be a non-polar solvent, a polar aprotic solvent, a polar protic solvent, or combinations thereof. In some embodiments, the composition includes a polar aprotic solvent. Non-limiting examples of polar aprotic solvents include n-methyl-2-pyrrolidone (NMP), dimethylformamide (DMF), dimethylacetamide (DMA) and dimethyl sulfoxide (DMS). The amount of solvent in the composition can be, for example, at least about 95% by weight; at least about 99% by weight; at least about 99.5% by weight; or at least about 99.9% by weight. The concentration of the one or more polyanthrylenes in the composition can be, for example, about 1 mg/L to about 200 mg/L; about 5 mg/L to about 120 mg/L; about 10 mg/L to about 90 mg/L; about 20 mg/L to about 70 mg/L; or about 40 mg/L to about 60 mg/L.

The composition may, in some embodiments, be in the form of a solid. For example, a solid form of the polyanthrylene can be obtained by precipitating or drying the polyanthrylene from solution (e.g., solvent casting). The solid composition can include amorphous or semi-crystalline forms of the polyanthrylene. In some embodiments, the one or more polyanthrylenes are blended with one or more polymers. Generally, any inert polymer can be blended with the polyanthrylenes; such inert polymers can be, for example, acrylics, polyolefins, polyamides, polyesters, polysulfones, fluoropolymers, vinyl polymers, and the like. For example, the composition can be a blend of a compound of Formula XVIII and polysulfone. This blend can by prepared, for example, by solvent casting to form a film. The amount of the polymer in the composition is not particularly limited and can be, for example, at least about 10% by weight; at least about 30% by weight; at least about 70% by weight; at least about 90% by weight; at least about 95% by weight; at least about 97% by weight; or at least about 99% by weight.

The composition can, in some embodiments, exhibit electrical conductivity. For example, the composition can exhibit a conductivity of about $1 \times 10^{-9}$ S·cm$^{-1}$. In some embodiments, the composition can exhibit a conductivity of about $1 \times 10^{-10}$ S·cm$^{-1}$ to about $1 \times 10^{-5}$ S·cm$^{-1}$. The composition can, in some embodiments, exhibit electrical conductivity when doped with an effective amount of dopant. For example, the composition can exhibit a conductivity of about $2.3 \times 10^{-3}$ S·cm$^{-1}$ when doped with iodine vapor. In some embodiments, the composition exhibits a conductivity of at least about $10^{-8}$ S×cm$^{-1}$ when doped with an effective amount of dopant. In some embodiments, the composition exhibits a conductivity of at least about $10^{-7}$ S·cm$^{-1}$ when doped with an effective amount of dopant. In some embodiments, the composition exhibits a conductivity of at least about $10^{-6}$ S·cm$^{-1}$ when doped with an effective amount of dopant. In some embodiments, the composition exhibits a conductivity of at least about $10^{-5}$ S·cm$^{-1}$ when doped with an effective amount of dopant. In some embodiments, the composition exhibits a conductivity of at least about $10^{-3}$ S·cm$^{-1}$ when doped with an effective amount of dopant. In some embodiments, the composition exhibits a conductivity of at least about $10^{-2}$ S·cm$^{-1}$ when doped with an effective amount of dopant. Non-limiting examples of dopants include halogenated compounds, such as iodine, bromine, chlorine, iodine trichloride; protonic acids such as sulfuric acid, hydrochloric acid, nitric acid, perchloric acid; Lewis acids, such as aluminum trichloride, ferric trichloride, molybdenum chloride; and organic acids, such acetic acid, trifluoracetic acid, and benzenesulfonic acid. In some embodiments, the dopant is iodine.

The composition can also exhibit fluorescence when exposed to radiation. In some embodiments, the composition can exhibit green or blue emission when exposed to blue or ultraviolet radiation. The green or blue emission can, for example, have a wavelength of peak emission of about 380 nm to about 650 nm. In some embodiments, the green or blue emission has a wavelength of peak emission of about 475 nm to about 525 nm. The blue or ultraviolet radiation may, for example, have a peak wavelength of about 380 nm to about 450 nm. Specific examples of peak emission wavelengths include about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, and ranges between any two of these values.

Method of Making Compositions Including Polyanthrylene

Some embodiments disclosed herein include a method of making one or more polyanthrylenes. Any one or more of the polyanthrylenes described in the present application can be prepared using this process. The method can include, for example, forming a composition comprising at least one oxidizing agent, at least one co-catalyst and anthracene; and maintaining the composition under conditions effective to covalently bond two or more anthracenes to form one or more polyanthrylenes.

The operation of forming the composition is not particularly limited. Any suitable method of combining the ingredients is within the scope of the present application. For example, the oxidizing agent can be combined (e.g., mixed or dissolved) in a first solvent, and anthracene can be combined (e.g., mixed or dissolved) in a second solvent. The solution can then be combined by dropwise or continuous addition of one of the mixtures to the other. The first and second solvents can be the same or different. In some embodiments, the first solvent is at least partially immiscible in the second solvent. In some embodiments, the oxidizing agent is soluble in the first solvent. In some embodiments, anthracene is soluble in both the first and second solvents. Non-limiting examples for the first solvent include $CH_3NO_2$, $C_6H_5NO_2$, $CHCl_3$, and mixture thereof. Non-limiting examples for the second solvent include nitro-alkane, halogenated alkane, alkane, and mixture thereof. In some embodiments, the second solvent can be $CH_3NO_2$, $CH_2Cl_2$, n-Hexane, $CH_3CH_2NO_2$, $CH_3CH_2Cl_2$, and mixture thereof.

Without being bound to any particular theory, it is believed that the polyanthrylene is formed by dehydrogen coupling between two or more anthracenes. Thus, oxidative agents that can dehydrogenate and dissolve in the solvent system (e.g., $CH_3NO_2$—$CH_2Cl_2$) without excessive side-reactions could be selected as the oxidizing agent. In some embodiments, the oxidizing agent is a Lewis acid. Examples of suitable oxidizing agents include, but are not limited to, $FeCl_3$, $AlCl_3$—$CuCl_2$, $TiCl_4$, $MoCl_5$, $SbCl_5$, $AsF_5$, and any combination thereof.

In some embodiments, the co-catalyst can be the solvent in which the polymerization of anthracene occurs, such as nitroalkane, halogenated alkane, alkane, or mixture thereof. In some embodiments, the co-catalyst can be $CH_3NO_2$, $CH_2Cl_2$, n-hexane, $CH_3CH_2NO_2$, $CH_3CH_2Cl_2$, or mixture thereof. In some embodiments, the co-catalyst can be $CH_2Cl_2$—$CH_3NO_2$. Without being bound to any particular theory, it is believed that Lewis acids can act as an oxidizing agent as well as a co-catalyst in the polymerization of anthracene.

The molar ratio of the oxidizing agent to anthracene in the composition can be, for example, at least about 1:1; at least about 2:1; at least about 3:1; at least about 4:1; at least about 5:1; at least about 7:1; at least about 8:1; at least about 9:1; at least about 10:1; at least about 11:1; at least about 12:1; at least about 13:1; at least about 14:1; at least about 15:1; at least about 16:1; at least about 17:1; or at least about 18:1. The molar ratio of the oxidizing agent to the total amount of anthracene in the composition can be, for example, less than or equal to about 20:1; less than equal to about 15:1; less than or equal to about 12:1; less than equal to about 9:1; less than equal to about 6:1; less than equal to about 3:1; or less than equal to about 1:1. In some embodiments, the molar ratio of the oxidizing agent to anthracene in the composition is about 7:1 to about 9:1.

In some embodiments, at least about 90% by weight of the total amount of aromatic compounds in the composition are anthracene. In some embodiments, at least about 95% by weight of the total amount of aromatic compounds in the composition are anthracene. In some embodiments, at least about 99% by weight of the total amount of aromatic compounds in the composition are anthracene. In some embodiments, substantially all of the total amount of aromatic compounds in the composition is anthracene.

After forming the composition having the oxidizing agent and anthracene, the composition can be maintained at conditions effective to form polyanthrylene. For example, the composition can be maintained at about atmospheric pressure and a temperature of about 10° C. to about 80° C. In some embodiments, the temperature can be about 10° C. to about 60° C. In some embodiments, the temperature can be about 15° C. to about 50° C. Non-limiting examples of the temperature include about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., and ranges between any two of these values. In some embodiments, the temperature can be about 20° C.

The composition can be maintained at the conditions for a period of time sufficient to obtain polyanthrylene. The composition, for example, can be maintained at the conditions for at least about 0.1 hour, at least about 0.5 hour, at least about 1 hour; at least about 3 hours; at least about 5 hours; at least about 10 hours; at least about 15 hours; at least about 20 hours; at least about 24 hours; or longer. The composition, for example, can be maintained at the conditions for less than or equal to about 100 hours; less than or equal to about 50 hours; less than or equal to about 30 hours; less than or equal to about 20 hours, less than or equal to about 10 hours, or less than or equal to about 5 hours.

The method can also optionally include isolating the polyanthrylene from the composition. For example, the polyanthrylene can be isolated by centrifuging the composition to obtain one or more polyanthrylenes within the precipitate. The polyanthrylene can be subject to various other optional treatments, such as washing, doping, dedoping, and the like.

The yield of the one or more polyanthrylenes using the method will vary depending upon various factors, such as the temperature and the like. In some embodiments, the method yields at least about 40% by weight of the one or more polyanthrylenes relative to a total amount of anthracene in the composition. In some embodiments, the method yields at least about 60% by weight of the one or more polyanthrylenes relative to a total amount of anthracene in the composition. In some embodiments, the method yields at least about 70% by weight of the one or more polyanthrylenes relative to a total amount of anthracene in the composition. In some embodiments, the method yields at least about 80% by weight of the one or more polyanthrylenes relative to a total amount of anthracene in the composition.

Methods and Apparatuses for Emitting Light

Some embodiments of the present application include methods and apparatuses for producing light.

A method of producing light can include exposing a composition to a blue or ultraviolet radiation, where the composition includes one or more polyanthrylenes. The method of producing light can include any one or more of the compositions described in this application. The blue or ultraviolet radiation can, for example, have a peak wavelength of about 380 nm to about 650 nm. In some embodiments, the method produces blue or green light. For example, the blue or green emission can have a wavelength of peak emission of about 380 nm to about 550 nm. In some embodiments, the blue or green emission can have a wavelength of peak emission of about 475 nm to about 525 nm. Specific examples of peak wavelengths include about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, and ranges between any two of these values.

FIG. 1 depicts an illustrative embodiment of a lighting apparatus that is within the scope of the present application. Lighting apparatus 100 includes substrate 110 having a light source 120 disposed above substrate 110. The light source can be coupled to an electric source and configured to emit blue or ultraviolet radiation. For example, the light source can be an indium gallium nitride (InGaN) semiconductor, ultraviolet bulb, and ultraviolet laser (e.g., He—Cd laser, N$_2$ laser, and Kr/Ar ion laser). Composition 130 is disposed next to light source 120 and configured to receive at least a portion of the radiation from light source 120. Composition 130 can be a powder dispersed in encapsulant resin 140. For example, encapsulant resin 140 can be an epoxy. As an alternative, the composition can be a film disposed above the light source (not shown).

In some embodiments, the apparatus includes: a light source configured to emit an ultraviolet or blue radiation; and a composition configured to receive at least a portion of the radiation emitted from the light source, where the composition includes one or more polyanthrylenes. The composition can include one or more polyanthrylenes as described in the present application.

The polyanthrylene compositions of the present application can also be included in an organic light emitting diode (OLED). OLEDs are well-known in the art. For example, U.S. Pat. No. 6,322,910 discloses various configurations for OLEDs. A typical OLED can include a light emitting layer disposed between a cathode and anode. A current flow between the cathode and anode can result in electrons recombining with electron holes in the light emitting layer. This recombination can result in emission. Thus, for example, the light emitting layer can include any one or more of the polyanthrylene compositions described in the present application. In some embodiments, the OLED can include multiple emissive layers.

Figure 2:
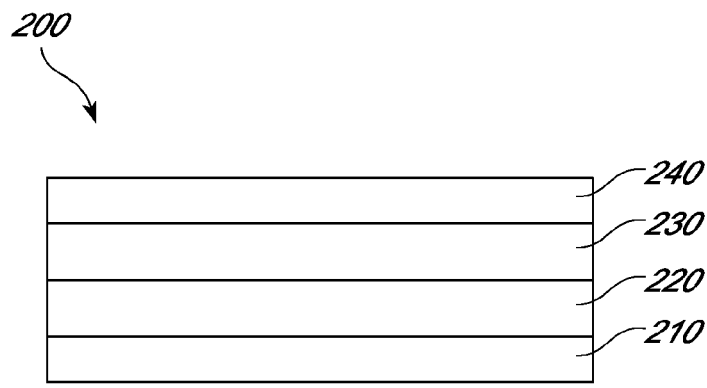
FIG. 2 depicts an illustrative embodiment of an apparatus for detecting ferric ions that is within the scope of the present application (not to scale).

FIG. 2 is an illustrative embodiment of an organic light emitting diode that is within the scope of the present application. OLED 200 includes anode 210 having conducting layer 220 above anode 210. Emissive layer 230 is disposed between conductive layer 220 and cathode 240. The anode can be, for example, indium tin oxide (ITO), which can optionally be disposed on a transparent substrate (e.g., glass) (not shown). Meanwhile, metals with low work functions, such as barium or calcium, can be used to form the cathode. The conductive layer can be a conductive polymer, such as poly(3,4-ethylenedioxythiophene) poly(styrenesulfonate) (PEDOT:PSS). The emissive layer can include any one or more of the polyanthrylene compositions described in the present application.

Methods and Apparatuses for Detecting Iron

Some embodiments of the present application include methods and apparatuses for detecting iron, for example ferrous ions (sometimes written as Fe(II) or $Fe^{2+}$) or ferric ions (sometimes written as Fe(III) or $Fe^{3+}$) from a sample. Without being bound to any particular theory, it is believed that ferrous ions in aqueous solution are unstable and can be easily and quickly oxidized into ferric ions by oxygen in the air, and ferric ions can quench fluorescence of the polyanthrylene compositions described in the present application. Thus, if the composition exhibits reduced fluorescence, this can be correlated with exposing the composition to iron, for example a ferric ion (Fe(III)) or a ferrous ion (Fe(II)).

In some embodiments, a method for detecting ferric ions includes: (a) providing a sample suspected of containing one or more ferric ions; (b) contacting the sample with a composition having one or more polyanthrylenes to form a mixture; (c) exposing the mixture to a radiation effective to produce fluorescence from the mixture; and (d) measuring the amount of fluorescence produced by the mixture. The composition can be any one or more of the polyanthrylene compositions described in the present application. For example, the composition can include the compound of Formula XVIII, the compound represented by Formula XIX, the compound represented by Formula XX, the compound of Formula XXI, the compound of Formula XXII, the compound of Formula XXIII, the compound of Formula XXV, the compound of Formula XXVI, the compound of Formula XXVII, and the compound of Formula XXVIII disclosed above.

In some embodiments, the produced fluorescence is greater in the absence of iron than in the presence of iron. In some embodiments, the produced fluorescence is greater in the absence of ferric ions than in the presence of ferric ions. The fluorescence can be measured, for example, by measuring the fluorescence intensity at a pre-determined color or wavelength. For example, the intensity of emission at a wavelength of about 502 nm can be measured. In some embodiments, the radiation effective to produce fluorescence from the composition is a blue or ultraviolet radiation.

Figure 3:
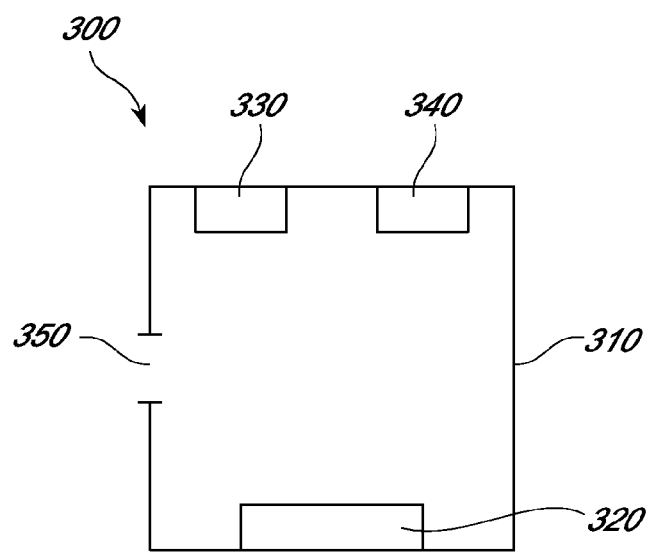
FIG. 3 depicts an illustrative embodiment of an apparatus for detecting ferric ions that is within the scope of the present application (not to scale).

FIG. 3 depicts an illustrative embodiment of an apparatus for detecting ferric ions that is within the scope of the present application. Apparatus 300 can include housing 310 that contains composition 320, light source 330, light detector 340, and port 350. Composition 320 can include any one or more of the polyanthrylene compositions described in the present application. Light source 330 is configured to emit radiation effective to produce fluorescence from copolymer film 320. For example, light source 330 can be an InGaN semiconductor that emits blue or ultraviolet radiation. Light detector 340 can be configured to measure light emission from composition 320. Port 350 can be configured to receive a sample into the housing. Thus, for example, a sample suspected of containing one or more ferric ions can be placed into housing 310 via port 350, so that the sample contacts composition 320. Light source 330 can then emit light and the fluorescence from composition 320 is detected by light detector 340. The amount of fluorescence can then be correlated with the presence of ferric ions in the sample.

In some embodiments, the apparatus for detecting iron, such as ferric ions, includes a processor coupled to at least the light source and light detector (not shown). The processor can be configured to synchronize both emitting light from the light source and detecting fluorescence with the light detector. The processor can also receive measurement data from the light detector and automatically correlate this data with the presence of iron, such as ferric ions.

Various concentrations of iron, such as ferric ions, can be detected by any one or more of the polyanthrylene compositions described in the present application. In some embodiments, the sample is an aqueous sample. In some embodiments, the sample is an environmental sample. In some embodiments, the sample is ocean water. The concentration of the ferric ion in the sample can be from about $10^{-9}$ mol/L (i.e., $10^{-9}$ M) to about $10^{-3}$ M, from about $10^{-9}$ M to about $10^{-4}$ M, from about $10^{-8}$ M to about $10^{-5}$ M, from about $10^{-7}$ M to about $10^{-6}$ M, and ranges between any two of these values. In some embodiments, the concentration of the ferric iron in the sample is no more than about $10^{-4}$ M. In some embodiments, the concentration of the ferric ion is no more than about $10^{-6}$ M. In some embodiments, the concentration of the ferric ion in the sample is less than about $10^{-7}$ M. In some embodiments, the concentration of the ferric ion in the sample is about $10^{-8}$ M. In some embodiments, the concentration of the ferric ion in the sample is about $10^{-9}$ M.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

EXAMPLES

Additional embodiments are disclosed in further detail in the following examples, which are not in any way intended to limit the scope of the claims.

Example 1

Preparation of Polyanthrylene (PAn)

The synthesis of polyanthrylene (PAn) was carried out by a chemical oxidative dehydrogenation polymerization of anthracenes (An) in $CH_3NO_2$—$CH_2Cl_2$ mixture.

A typical synthesis procedure of PAn included dissolving anthracene (800 mg, 4.49 mmol) in 30 mL $CH_2Cl_2$ in a conical flask in a water bath at 20° C. An oxidant solution was prepared by dissolving the oxidant $FeCl_3$ (6552 mg, 40.4 mmol) in 30 mL $CH_3NO_2$ at 20° C. Next, the oxidant solution was added all at once into the anthracene solution in water bath at 20° C., and the reaction mixture was magnetically stirred at 20° C. for 6 hours. Besides the role of the oxidative agent, $FeCl_3$ also functioned as a co-catalyst in the polymerization process. The other co-catalyst was $CH_3NO_2$—$CH_2Cl_2$ which was also used as the solvent for polymerization reaction. The polymerization was terminated by adding 60 mL ethanol to the reaction mixture. The polymer particles were precipitated and isolated from the reaction mixture by a centrifugal precipitation method, and then washed repeatedly with 95% ethanol until the filtrate became colorless. The polymer particles were subsequently washed with deionized water until the filtrate showed negative in a test for Fe(III) and Fe(II) ions by using 100 mM $K_4Fe(CN)_6$ and 50 mM $K_3Fe(CN)_6$ as color indicators, respectively. The dark brown powder as a virgin PAn salt was obtained after drying under air atmosphere at 80° C. For the purpose of removing of possible dopant impurities, the virgin PAn salt was washed successively with 1 M HCl solution, deionized water, 200 mM aqueous ammonia and deionized water, again until a negative test for Fe(III) and Fe(II) was obtained. The de-doped polymer particles as a pure PAn base were left to dry under air atmosphere at 80° C. for 3 days, giving a synthetic yield of 66.3%. Iodine vapor doping was carried out in closed graded tube (5 mL) containing 30 mg powdered virgin PAn and 150 mg solid iodine at a constant temperature of 80° C. under atmospheric pressure for a whole day. Direct contact between the PAn powders and the iodine particles was avoided.

The anthracene polymerization was followed by an open circuit potential (OCP) in situ tracking method using a saturated calomel electrode (SCE) and a platinum sheet electrode as the reference electrode and the working electrode respectively.

Example 2

UV-Vis, Fluorescence Excitation and Emission Spectra

PAn particles were prepared according to Example 1. UV-vis and fluorescence spectra of those PAn particles at a concentration of 20 mg/L in N-methyl-2-pyrrolidone (NMP) aqueous medium were respectively recorded by using a 760CRT double-beam UV-vis spectrophotometer and a 970CRT fluorospectrophotometer. These results are shown in FIGS. 4a-c.

Figure 4A:
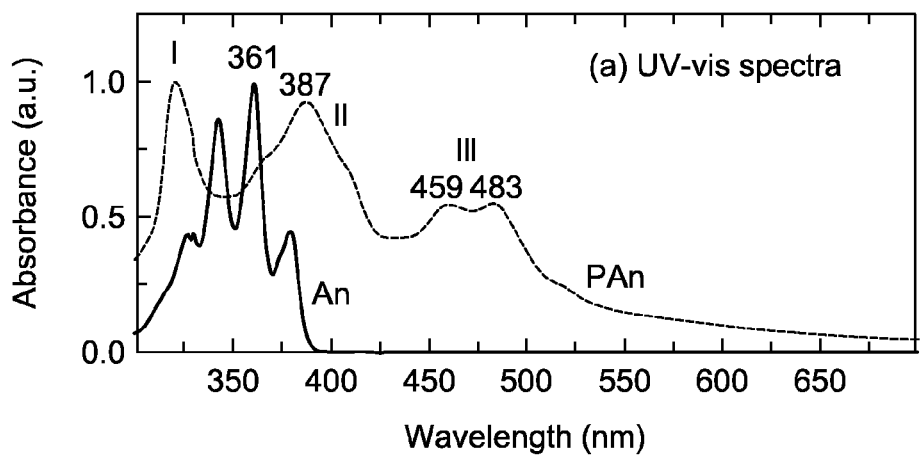
FIG. 4a-c shows the UV-visible, fluorescence excitation and emission spectra of anthracene (An) and polyanthrylene (PAn) solutions in NMP at concentration of 20 mg/L.
Figure 4B:
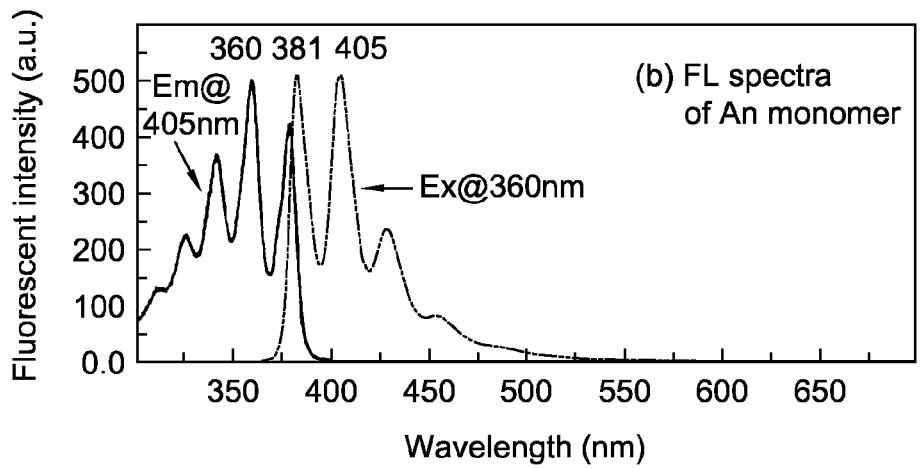
Figure 4C:
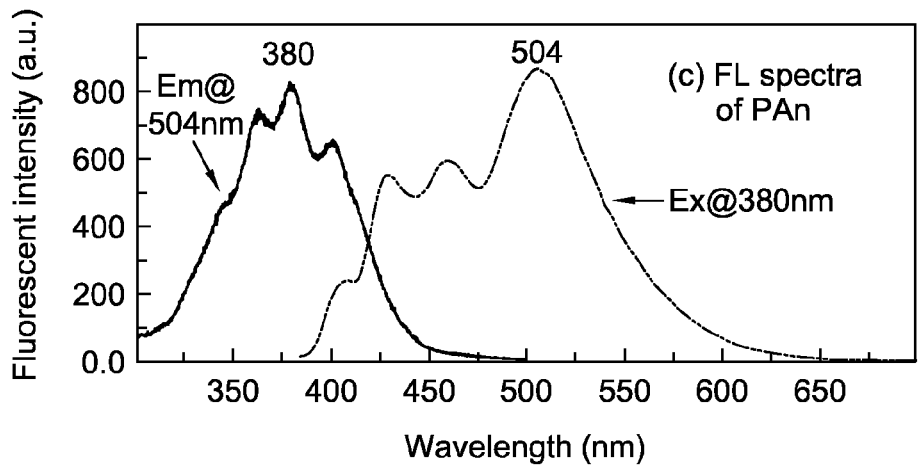

FIG. 4a shows the large difference between the UV-vis spectra of anthracene and that of PAn. The broad emission band exhibited by PAn with a maximum at 504 nm (excited at 380 nm) and a large Stokes shift of 117 nm demonstrates a rigid semi-ladder structure of PAn (see FIGS. 4b-c). Moreover, PAn showed 1.70 times stronger emission and 2.70 times higher Stokes shift than anthracene which emits only blue light, demonstrating that PAn is a strong green emitter with a high Stokes shift, and thus can be useful as a naked-eye fluorescent sensor.

Furthermore, it was found that the PAn prepared was a strong color light emitter that emitted blue light in low dielectric constant solvents including n-hexane, benzene, n-butanol, THF, ethanol, and chloroform. Also, the PAn was observed to emit green light in high dielectric constant solvents such as acetone, NMP, DMF, and DMSO.

Example 3

MALDI-TOF Mass Spectra

Figure 5:
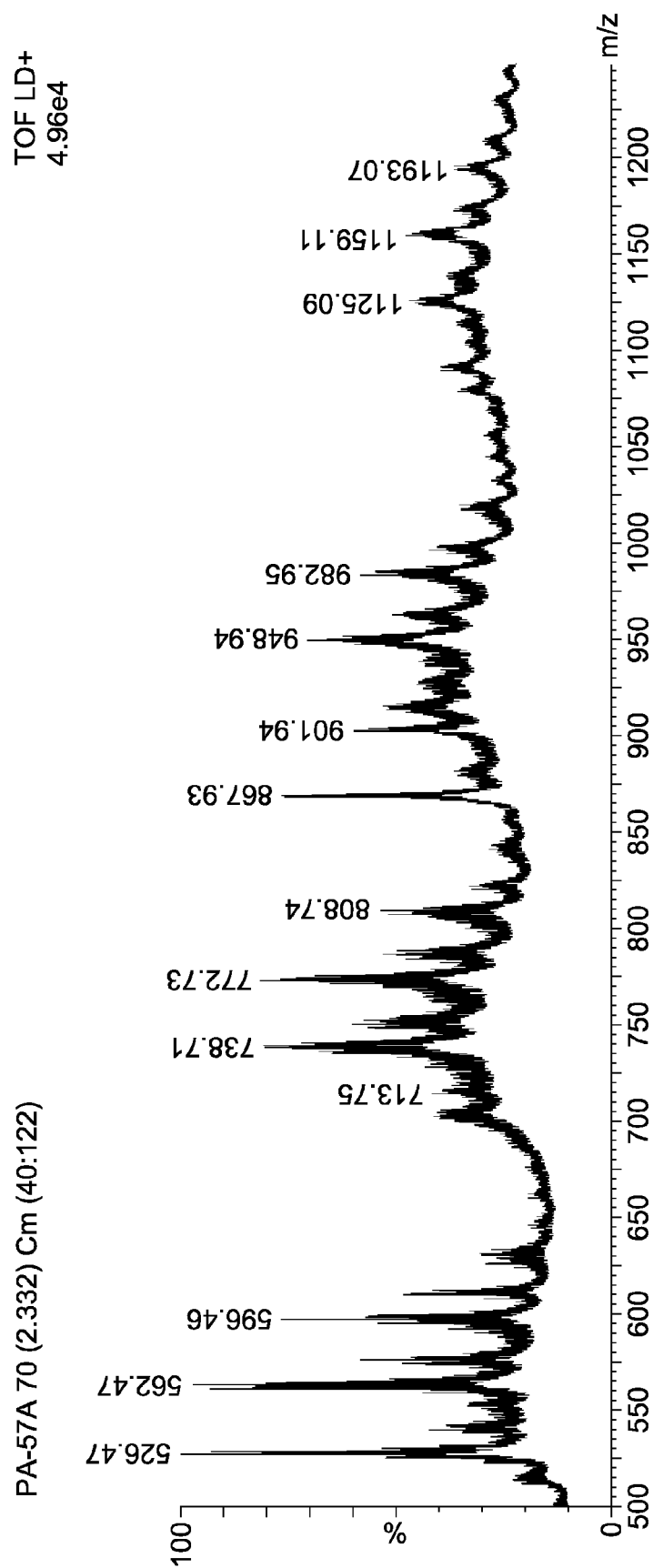
FIG. 5 shows the MALDI-TOF mass spectra for the polyanthrylene (PAn) prepared with $FeCl_3$/An molar ratio of 9:1.

PAn particles were prepared with oxidant $FeCl_3$/anthracene molar ratio of 9:1 according to the general procedure described in Example 1. The matrix assistant laser desorption ionization time of flight mass spectrum (MALDI-TOF MS) of those PAn particles was recorded on a Waters Micromass MALDI micro MX mass spectrometer with sinapinic acid as matrix. The results are shown in FIG. 5. Structural assignments of the peaks appearing in the MALDI-TOF mass spectra of the PAn are shown in Table 1, demonstrating that the obtained PAn is composed of 3 to 11 repeat anthrylene units containing semi-ladder structures.

TABLE 1
Structural assignments of the peaks appearing in the MALDI-TOF mass spectra of the PAn
| m/z | Repeat unit n | Possible structures |
|---|---|---|
| 526.5 | 3 | 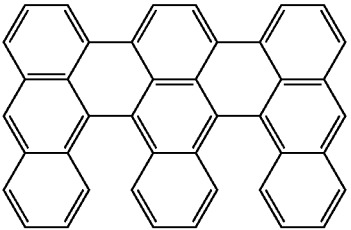 |
| 703 | 4 | 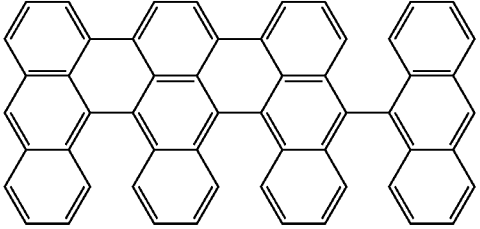 |
| 866.9 | 5 | 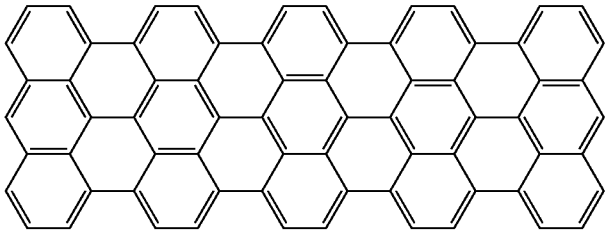 [SMILES: c1cc2cc3cccc4c5ccc6c7ccc8c9ccc%10c%11cccc%12cc%13cccc%14c%15ccc%16c%17ccc%18c%19ccc%20c(c1)c2c(c34)c1c%20c%19c(c6c51)c1c%18c%17c(c8c71)c1c%16c%15c(c%10c91)c(c%13%14)c%12%11] |
| 1581.4 | 9 | 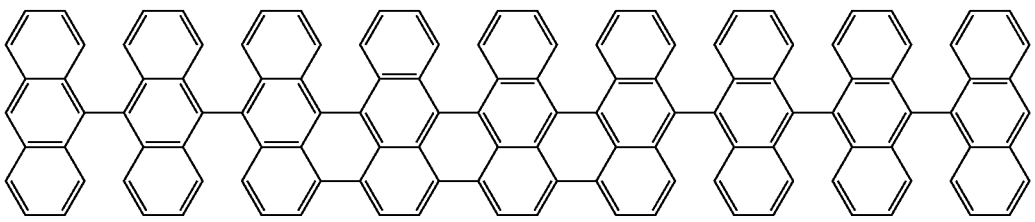 [SMILES: c1ccc2c(-c3c4ccccc4c(-c4c5ccccc5c(-c5c6ccccc6c6c7c5cccc7c5ccc7c8ccc9c%10cccc%11c(-c%12c%13ccccc%13c(-c%13c%14ccccc%14cc%14ccccc%13%14)c%13ccccc%12%13)c%12ccccc%12c(c%11%10)c%10c%11ccccc%11c(c8c9%10)c8c9ccccc9c6c5c78)c5ccccc45)c4ccccc34)c3ccccc3cc2c1] |
| 1758.0 | 10 | 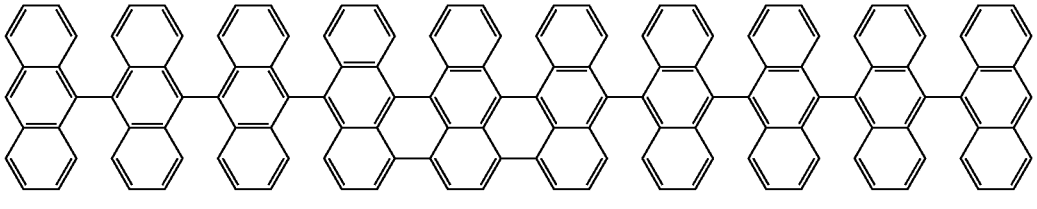 [SMILES: c1ccc2c(-c3c4ccccc4c(-c4c5ccccc5c(-c5c6ccccc6c(-c6c7ccccc7c7c8c6cccc8c6ccc8c9cccc%10c(-c%11c%12ccccc%12c(-c%12c%13ccccc%13c(-c%13c%14ccccc%14cc%14ccccc%13%14)c%13ccccc%12%13)c%12ccccc%11%12)c%11ccccc%11c(c%109)c9c%10ccccc%10c7c6c89)c6ccccc56)c5ccccc45)c4ccccc34)c3ccccc3cc2c1] |
| 1932.0 | 11 | 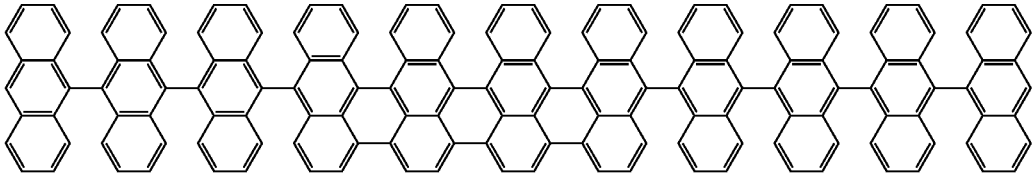 [SMILES: c1ccc2c(-c3c4ccccc4c(-c4c5ccccc5c(-c5c6ccccc6c(-c6c7ccccc7c7c8c6cccc8c6ccc8c9ccc%10c%11cccc%12c(-c%13c%14ccccc%14c(-c%14c%15ccccc%15c(-c%15c%16ccccc%16cc%16ccccc%15%16)c%15ccccc%14%15)c%14ccccc%13%14)c%13ccccc%13c(c%12%11)c%11c%12ccccc%12c(c9c%10%11)c9c%10ccccc%10c7c6c89)c6ccccc56)c5ccccc45)c4ccccc34)c3ccccc3cc2c1] |

Example 4

NMR Spectra

PAn particles were prepared according to Example 1. $^1$H 1D and $^1$H-$^1$H COSY 2D NMR spectra of the soluble portion of those PAn particles in DMSO-d6 were determined using a Bruker DQX-400 spectrometer. The results are shown in FIG. 6.

Figures 6A, 6B:
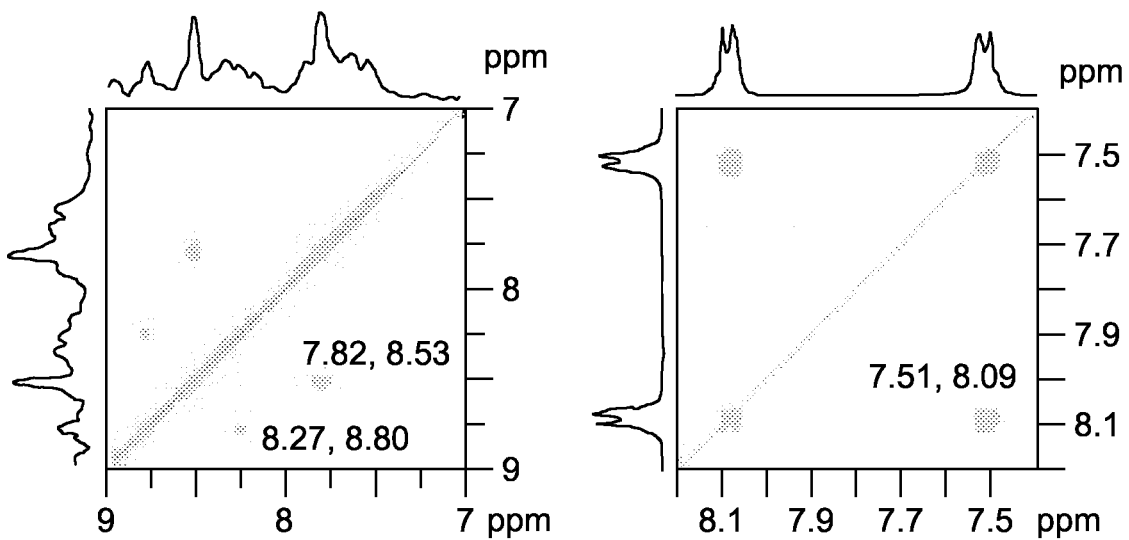
FIG. 6a-c shows the NMR spectra of An and PAn.
Figure 6C:
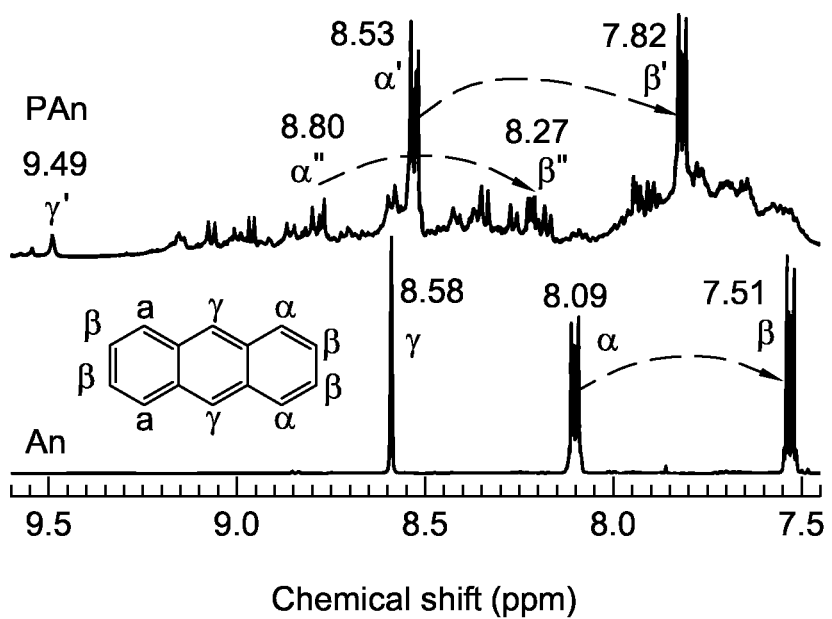

The PAn displayed much more complicated $^1$H NMR and $^1$H-$^1$H COSY NMR spectra than anthracene. For example, there were two cross peaks in the $^1$H-$^1$H 2D COSY spectrum of the PAn (FIG. 6a) as compared to a single cross peak in that of anthracene (FIG. 6b). The much weaker resonance peak due to γ-H in the $^1$H NMR spectrum of the PAn shown in FIG. 6c demonstrates that the oxidative coupling of anthracene rings occurred mainly at γ positions (9,10-positions). An additional weak cross peak (8.27, 8.80 ppm) shown in FIG. 6c further shows that the oxidative coupling of anthracene rings also occurred partly at α positions (1,4,5,8-positions), forming a semi-ladder structure.

Example 5

Elemental Analysis

PAn particles were prepared according to Example 1. The elemental analysis of those PAn particles was carried out using a VARIO EL3 elemental microanalyzer.

Elemental analysis showed that the C/H atomic ratio in the PAn was 1.79, which was larger than the C/H ratio of 1.75 for linear PAn (—$C_{14}H_8$-)n, indicating the existence of a semi-ladder structure in the PAn molecules.

Example 6

Electrical Conductivity

PAn particles were prepared according to Example 1. The bulk electrical conductivity of the PAn was measured from pressed pellets according to the two-electrode method on a UT70A multimeter at ambient temperature. The electrical conductivity for virgin PAn salt was determined to be $1.00 \times 10^{-9}$ S·cm$^{-1}$, and the electrical conductivity for iodine-doping PAn salt was determined to be $2.30 \times 10^{-3}$ S·cm$^{-1}$.

Example 7

Fluorescence Emission

Figure 7:
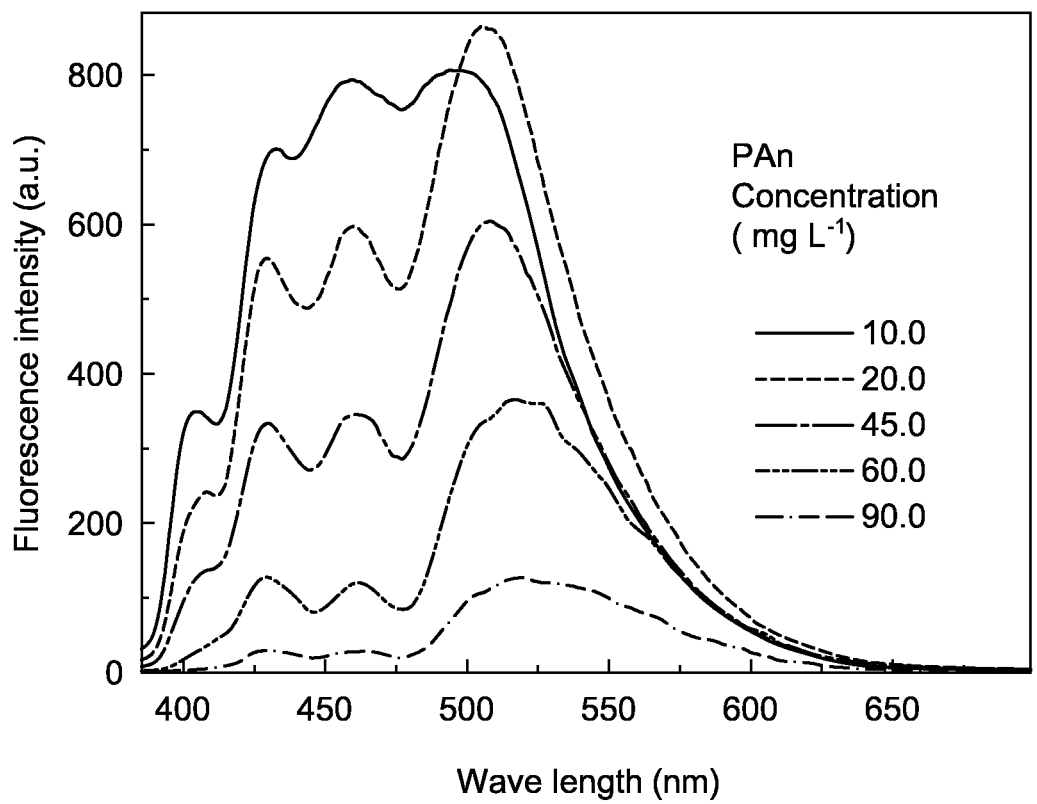
FIG. 7 shows fluorescence emission spectra (excited at 380 nm) of the PAn in NMP at various concentrations.

PAn particles were prepared according to Example 1. Fluorescence emission spectra of those PAn particles at a concentration of 10 mg/L, 20 mg/L, 45 mg/L, 60 mg/L or 90 mg/L in N-methyl-2-pyrrolidone (NMP) aqueous medium were respectively recorded using a 970CRT fluorospectrophotometer. The results are shown in FIG. 7.

This example shows that fluorescence emission intensity of the PAn solution depends on its concentration, and the strongest fluorescence emitting by the PAn solution in the concentration tested is in the concentration of 20 mg/L.

Example 8

Fluorescence Spectral Responses of PAn to Fe(III)

PAn particles were prepared according to Example 1. Those PAn particles were dissolved in NMP solution to make a PAn-NMP solution with the concentration of PAn at 25 mg/L. 4 mL of the PAn-NMP solution (the concentration of PAn at 25 mg/L) was mixed with 1 mL Fe(III) aqueous solution at a given concentration and the mixture solution was allowed to stand for 5 minutes at ambient temperature before a fluorescence measurement was performed. Using a constant excitation at 380 nm, the fluorescence emission intensity at 502 nm was used to establish a linear quantitative relation to the Fe(III) concentration for facilely sensing Fe(III). The results are shown in FIGS. 8-9.

Figure 8:
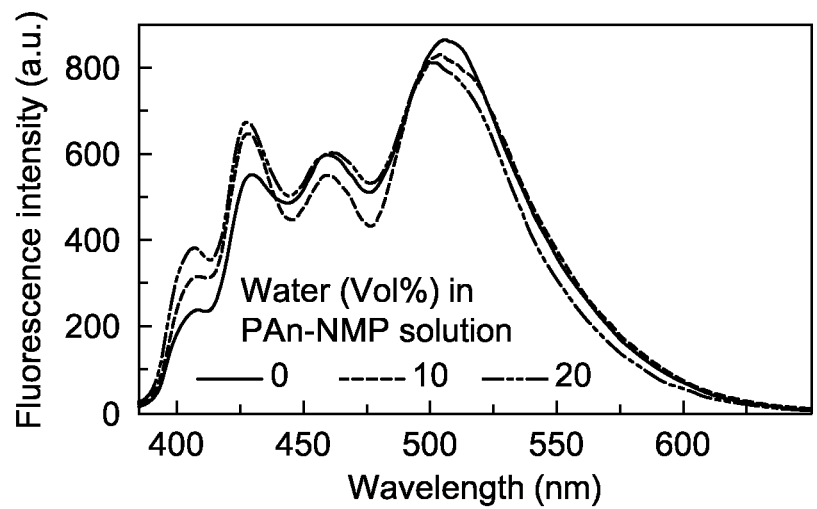
FIG. 8 shows fluorescent emission spectra of the PAn-NMP solutions containing three water contents.

FIG. 8 shows that the fluorescent emission intensity of the PAn only slightly reduced when 10~20 vol % water was added into the PAn-NMP solution, demonstrating that the fluorescent emission of the PAn is insensitive to a small amount of water in the solution system.

Figure 9:
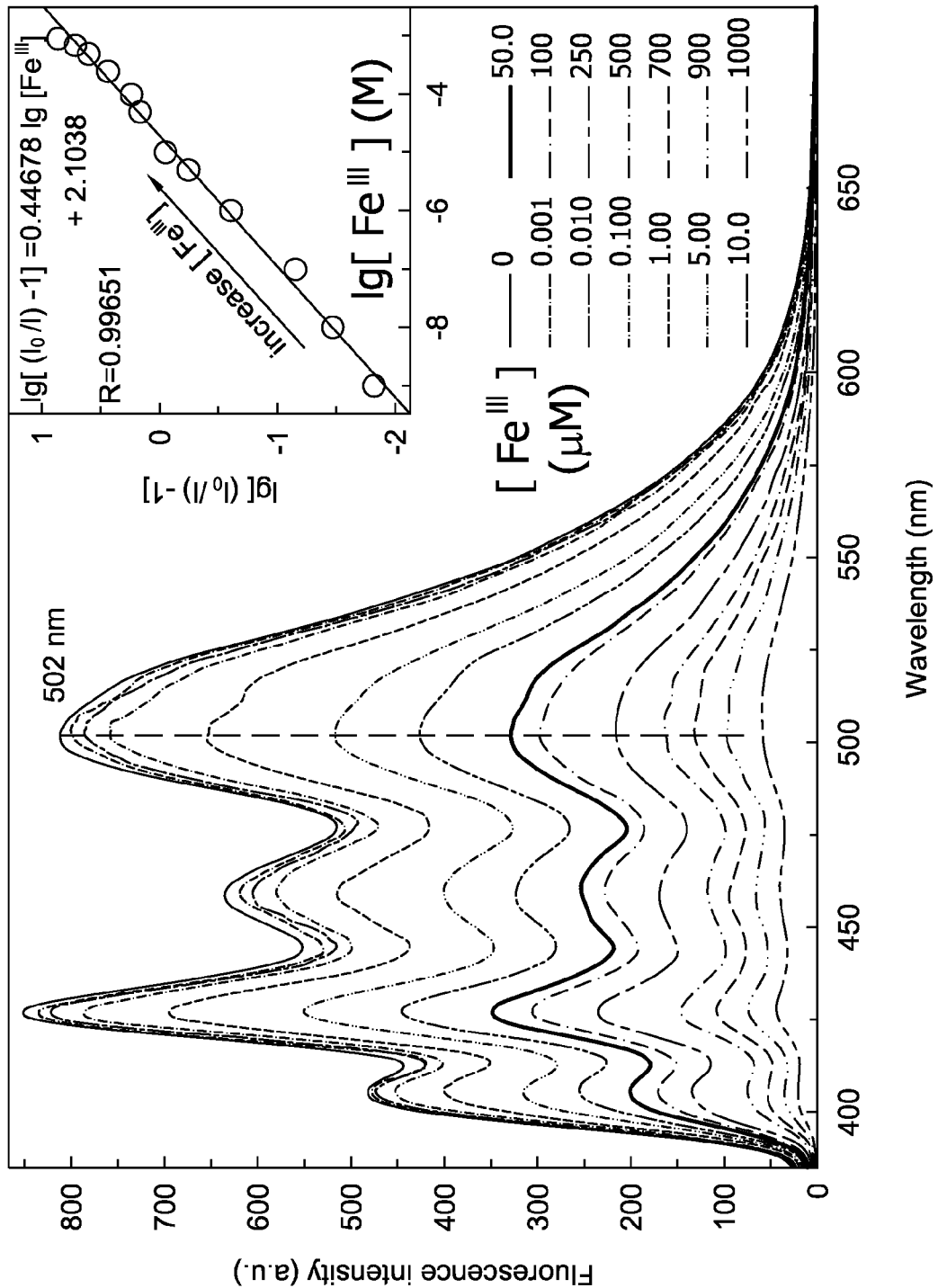
FIG. 9 shows fluorescence emission spectra (excited at 380 nm) for the same PAn solution after adding various aqueous solutions with different Fe(III) content. Inset: the modified Stern-Volmer plot. $I_0$ and I represent the emission intensities at 502 nm without and with the Fe(III) quencher, respectively.

FIG. 9 shows a quenching effect on the addition of ferric ion. For example, the quenching ratios $(1-I/I_0) \times 100\%$ of PAn fell between 1.47% and 92.8%, with no noticeable shift in its λmax of 502 nm as the Fe(III) concentration increased from $1.00 \times 10^{-9}$ to $1.00 \times 10^{-3}$ M. FIG. 9 inset further shows that in the Fe(III) concentration range of 0 μM to 1000 μM, a satisfactory linear correlation could be fitted, with a correlation coefficient R of 0.99651. These results demonstrate the exceptional sensitivity of the PAn-based chemosensor system in detection of ferric ions is at an ultralow nanomolar level (down to $1.00 \times 10^{-9}$ M).

Example 9

Ion Selectivity of PAn

PAn particles were prepared according to Example 1. Those PAn particles were dissolved in NMP solution to make a PAn-NMP solution with the concentration of PAn at 20 mg/L.

Potential Interfering Ions at Concentration of 1 mM

Figure 10A:
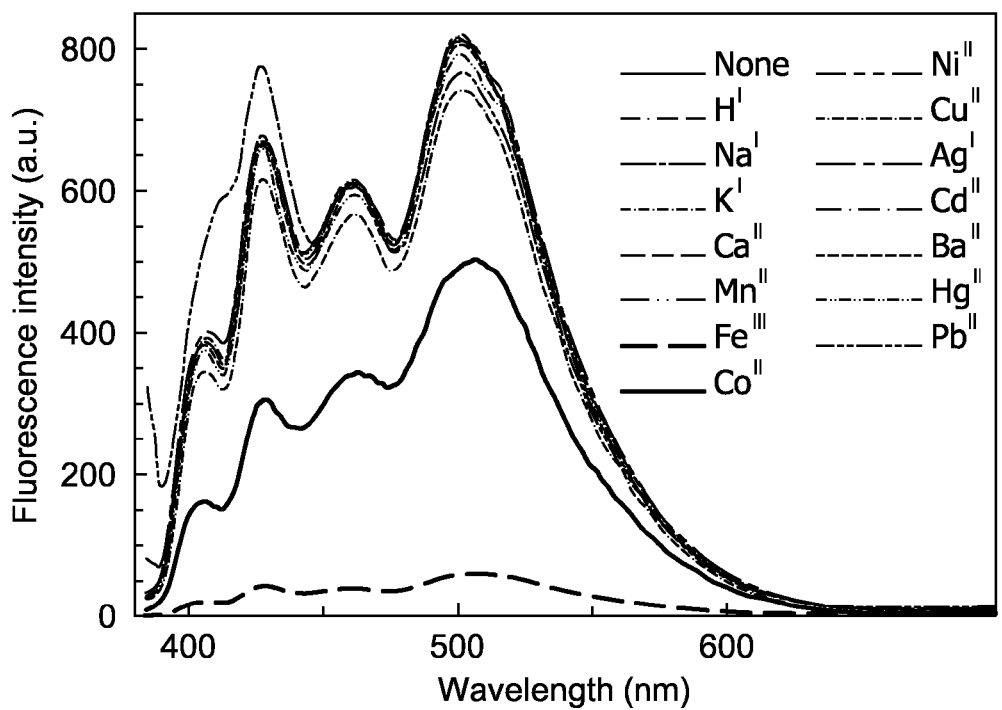
FIG. 10a-b shows fluorescence emission spectra (a), and fluorescence quenching efficiencies and metal-ion charge density (b) of the same PAn solution (PAn at concentration 20 mg/L) containing 1 mM different aqueous metal ions. $I_0$ and I refer to the emission intensity at 502 nm before and after adding metal ions.
Figure 10B:
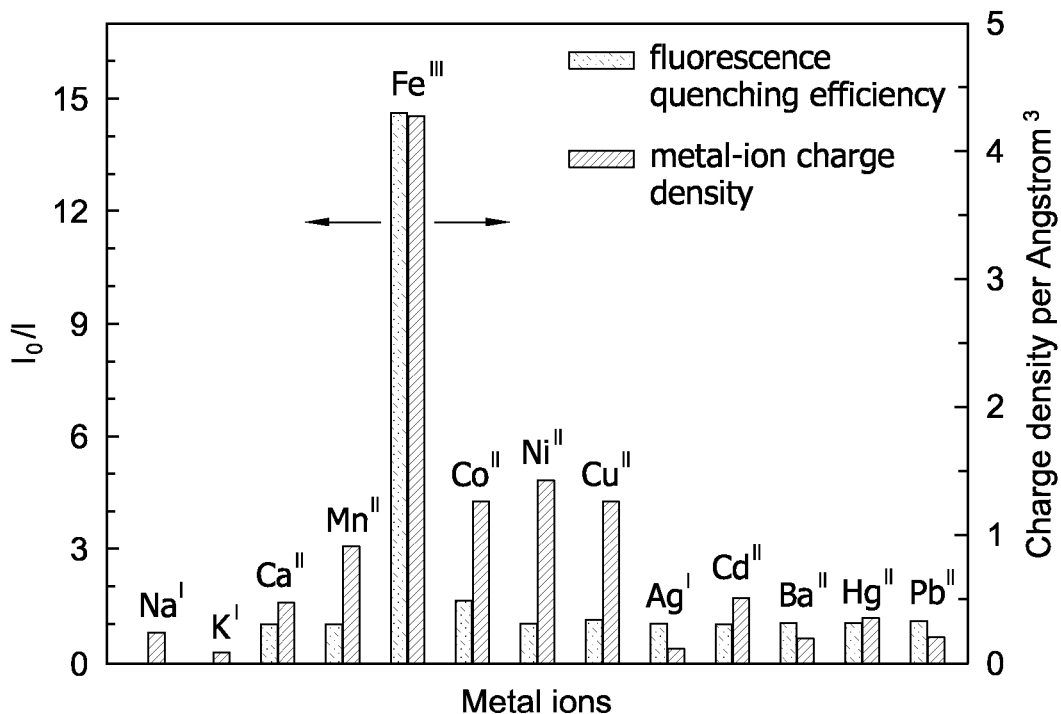

Solutions of various metal salts were prepared to investigate potential interferences in the detection of Fe(III) using PAn. Sixteen types of ions: H$^+$, Na(I), K(I), Ca(II), Mn(II), Co(II), Ni(II), Cu(II), Ag(I), Cd(II), Ba(II), Hg(II), Pb(II), Cl$^-$, NO$_3^-$, and SO$_4^{2-}$, at the concentration of 1 mM in the PAn-NMP solutions, were individually used to evaluate the ion selectivity of the PAn-based chemosensor. The variation of the fluorescence emission intensity of PAn-NMP solution containing a mixture of Fe(III) and those 16 types of ions was measured to evaluate the interference caused by those ions in the detection of Fe(III) ions. The degree of interference was evaluated by 502 nm intensity variation of corresponding fluorescence emission spectra. The results are shown in FIG. 10.

TABLE 2

The quenching degree and charge density of various types of cations to the PAn-based chemosensor

| | Metal ion | | | | | | |
|---|---|---|---|---|---|---|---|
| | H(I) | Na(I) | K(I) | Ca(II) | Mn(II) | Fe(III) | Co(II) |
| Quenching degree/% | 0 | 0 | 0 | 0.722 | 0.722 | 93.2 | 38.3 |
| $I_0/I$ | 0 | 0 | 0.00379 | 1.007 | 1.007 | 14.62 | 1.62 |
| Charge density/(Per Angstrom$^3$) | 1.91 | 0.26 | 0.1 | 0.49 | 0.93 | 4.31 | 1.28 |

| | Metal ion | | | | | | |
|---|---|---|---|---|---|---|---|
| | Ni(II) | Cu(II) | Ag(I) | Cd(II) | Ba(II) | Hg(II) | Pb(II) |
| Quenching degree/% | 2.90 | 8.71 | 0.722 | 0.355 | 0.722 | 1.82 | 5.95 |
| $I_0/I$ | 1.03 | 1.095 | 1.007 | 1.004 | 1.007 | 1.019 | 1.063 |
| Charge density/(Per Angstrom$^3$) | 1.45 | 1.28 | 0.12 | 0.52 | 0.2 | 0.36 | 0.21 |

FIG. 10 shows that $H^+$, Na(I), K(I), Ca(II), Mn(II), Ni(II), Cu(II), Ag(I), Cd(II), Ba(II), Hg(II), Pb(II), $Cl^-$, $NO_3^-$, and $SO_4^{2-}$ had no noticeable response to the fluorescence signal, and only Co(II) produced a slight quench. Accordingly, it demonstrates that the PAn chemosensor displays not only a highly sensitive fluorescence quenching response to Fe(III), but also an excellent selectivity against many metal ions, including Cu(II).

Interfering Effects of Co(II), Na(I), Ca(II) and Mg(II)

Figure 11A:
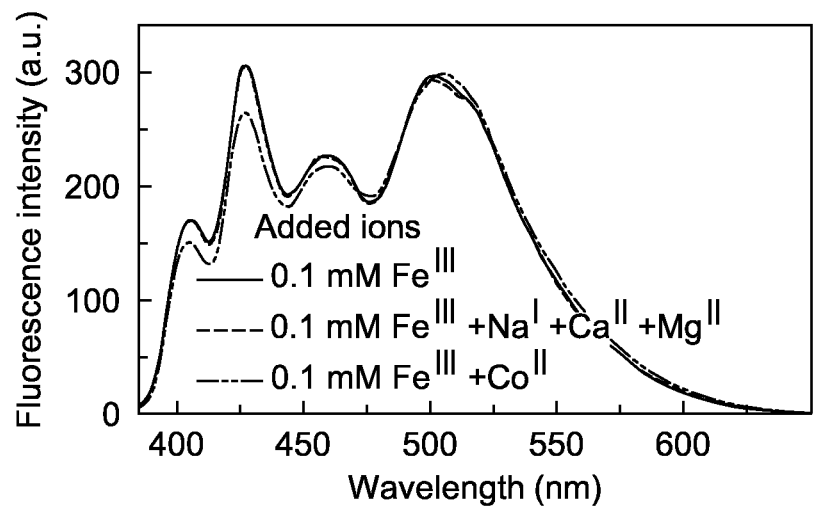
FIG. 11a-b shows fluorescent emission spectra of various PAn-NMP solutions (PAn at concentration 20 mg/L) with different content in metal ions.

The fluorescent quenching strength of a solution mixture of Co(II) (0.1 mM) and Fe(III) (0.1 mM) were measured. The results are shown in FIG. 11a. It was surprising that the co-existent Co(II) at the same concentration as the target ion Fe(III) resulted in negligible fluorescent and absorbance intensity change at 502 nm in almost the whole wavelength range, respectively, demonstrating that Co(II) does not significantly interfere with Fe(III) detection during the competition quenching process.

Figure 11B:
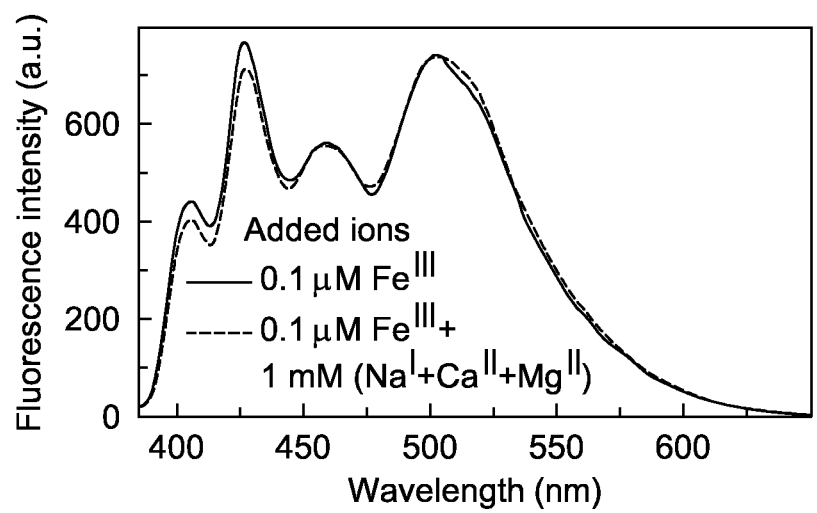

Similar measurements were conducted for two solutions with mixed Fe(III), Na(I), Ca(II) and Mg(II). In both solutions, the concentration of Fe(III) was 0.1 mM, whereas the concentration of each of the other ions (i.e., Na(I), Ca(II) and Mg(II)) is 0.1 mM in one solution and 1 mM in the other solution. The results are shown in FIG. 11b. FIG. 11b shows there is little fluorescent or absorbance change even if the concentration of Na(I), Ca(II) and Mg(II) ions are 10,000 times higher than that of Fe(III), demonstrating that the PAn has remarkably high selectivity towards Fe(III) and an excellent anti-interference ability against other metal ions.

Example 10

Detection of Fe(III) in Environmental Samples

PAn particles were prepared according to Example 1. Those PAn particles were used to detect iron content in environmental samples. Tap water was collected from an indoor tap in Tongji University, Shanghai, China. Residual water in the water pipe was discharged before collecting tap water for fluorescence quenching experiments without any pretreatment. River water sample was collected from the small river in the same university grounds and filtered three times to completely remove suspended solids and sediments. The concentration of various metal ions including Fe(III), Na(I), Ca(II), Cu(II), Zn(II), Cd(II), Hg(II) and Pb(II) in the water samples was determined by analyzing fluorescence spectra (excited at 380 nm) for the solution of PAn (20 mg/L) in NMP-water (4:1, v/v) after addition of pure water and actual water samples by a calibration curve obtained by this PAn chemosensor. To verify the sensitivity and accuracy of the results obtained by the PAn chemosensor, the concentration of the various metal ions were also determined using the inductively coupled plasma mass spectroscopy (ICP-MS) method which is presently one of the common methods for iron determination. The results are shown in Tables 3 and 4.

TABLE 3

The content of various metal ions (µM) in water samples measured by ICP-MS

| Water sample | Na(I) | Ca(II) | Fe(III) | Cu(II) | Zn(II) | Cd(II) | Hg(II) | Pb(II) |
|---|---|---|---|---|---|---|---|---|
| Tap water | 1683 | 1073 | 3.44 | 1.10 | 5.31 | 0.089 | <0.15 | <0.121 |
| River water | 5174 | 1870 | 0.897 | 0.853 | 1.56 | <0.018 | <0.15 | <0.121 |

TABLE 4

Concentration of Fe(III) in water samples (3 replicates)

| | Concentration of $Fe^{III}$ (µM) determined by | | | | | |
|---|---|---|---|---|---|---|
| | Fluorescence quenching using PAn | | | | | |
| Sample | $1^{st}$ | $2^{nd}$ | $3^{rd}$ | Average | ICP-MS | Relative error (%) |
| Tap water | 3.43 | 3.42 | 3.38 | 3.41 | 3.44 | −0.87 |
| River water | 0.910 | 0.907 | 0.929 | 0.915 | 0.897 | 2.04 |

As shown in Table 3, including Fe(III), a total of eight types of metal ions were detected in the water samples. Table 4 shows that the Fe(III) concentrations measured using PAn chemosensor were virtually identical to those detected by ICP-MS methods with very little relative error (−0.87%~2.04%) despite the existence of seven other metal ions in the water samples. Accordingly, this example shows that the PAn chemosensor can provide accurate and selective analysis of Fe(III) in water samples.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at lest one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for detecting ferric ions from a sample, the method comprising:
   providing a sample suspected of containing one or more ferric ions; and
   contacting the sample with a composition to form a mixture, wherein the composition comprises one or more polyanthrylenes, wherein the one or more polyanthrylenes each independently comprises at least two monomer units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, and any combination thereof:

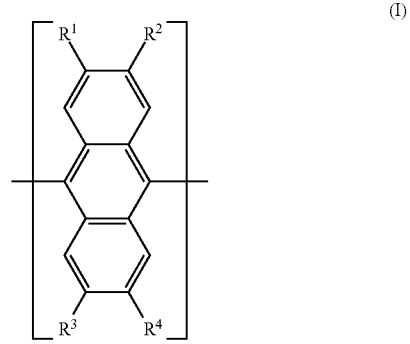

(I)

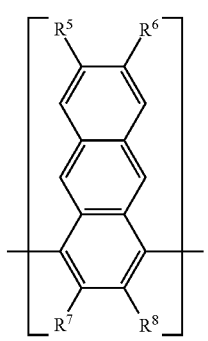 (II)
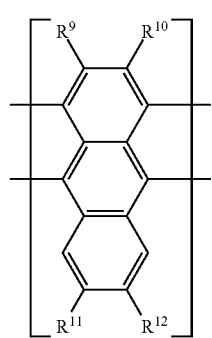 (III)
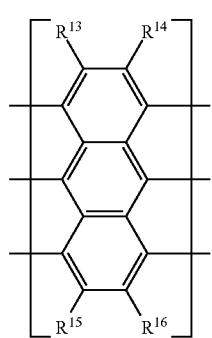 (IV)
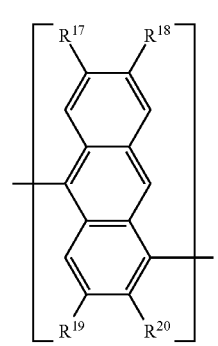 (V)
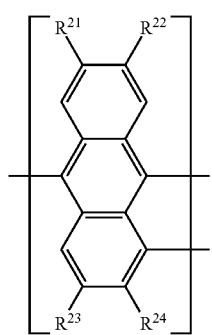 (VI)
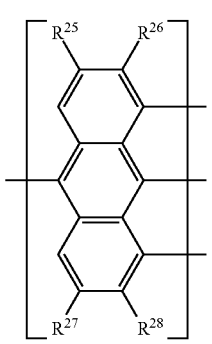 (VII)
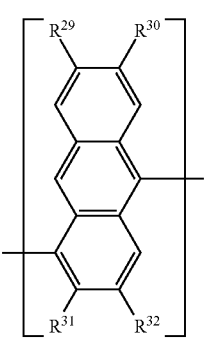 (VIII)
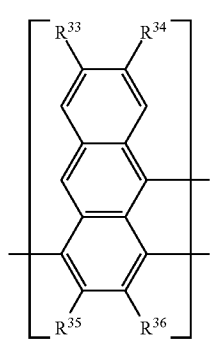 (IX)

(X) 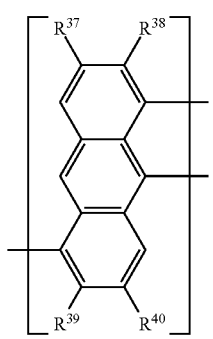

(XI) 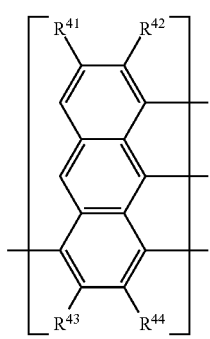

(XII) 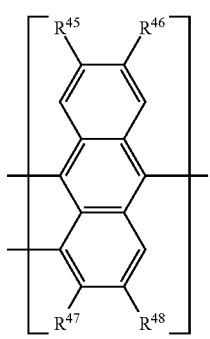

(XIII) 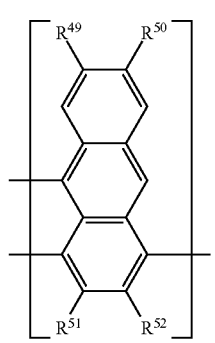

(XIV) 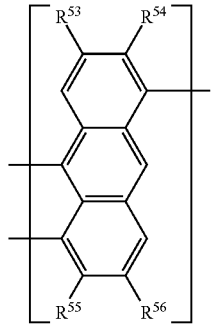

(XV) 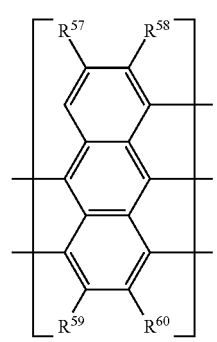

(XVI) 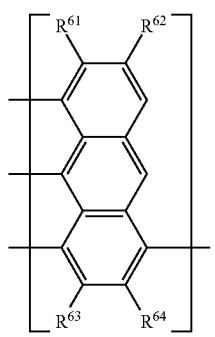

(XVII) 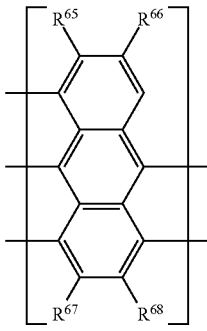

wherein $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}$, and $R^{68}$ are each independently hydrogen or an electron donating group, wherein at least one monomer unit in the one or more polyanthrylenes is not represented by Formula I;

exposing the mixture to a radiation effective to produce fluorescence from the mixture;

measuring the amount of fluorescence produced by exposing the mixture to the radiation; and determining the presence or absence of ferric ions in the sample based on the amount of fluorescence measured.

2. The method of claim 1, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, and $R^{68}$ are each independently hydrogen.

3. The method of claim 1, wherein the electron donating group is selected from the group consisting of —$CH_3$, —$CH_2CH_3$, —OH, —$OCH_3$, —$OCH_2CH_3$, —$N(CH_3)_2$, —$N(CH_2CH_3)_2$, and —SH.

4. The method of claim 1, wherein at least one of the one or more polyanthrylenes comprises at least three anthracene units each independently represented by a formula selected from the group consisting of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, and Formula XVII, and any combination thereof.

5. The method of claim 1, wherein at least one of the one or more polyanthrylenes has a molecular formula selected from the group consisting of $C_{42}H_{22}$, $C_{56}H_{30}$, $C_{70}H_{26}$, $C_{126}H_{68}$, $C_{140}H_{78}$, and $C_{154}H_{84}$.

6. The method of claim 5, wherein at least one of the one or more polyanthrylenes has a molecular formula of $C_{42}H_{22}$.

7. The method of claim 1, wherein at least one of the one or more polyanthrylenes includes a compound represented by Formula XVIII or Formula XIX:

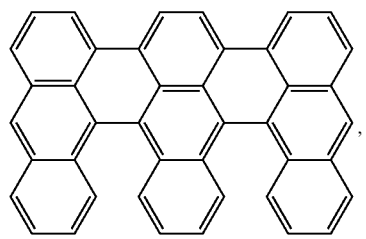

XVIII

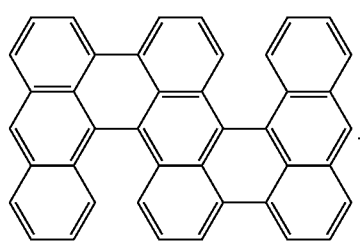

XIX

8. The method of claim 5, wherein at least one of the one or more polyanthrylenes has a molecular formula of $C_{56}H_{30}$.

9. The method of claim 8, wherein at least one of the one or more polyanthrylenes includes a compound represented by a formula selected from the group consisting of Formula XX, Formula XXI, Formula XXII, and Formula XXIII.

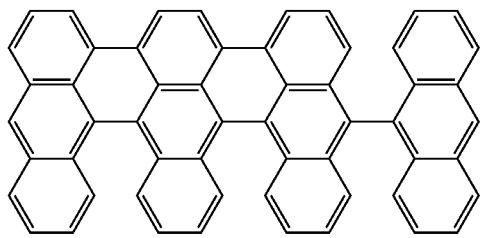

XX

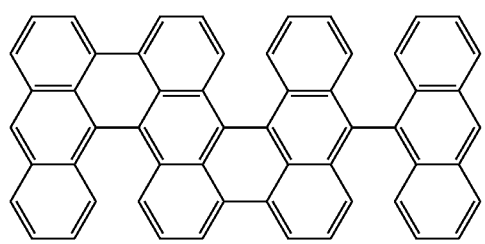

XXI

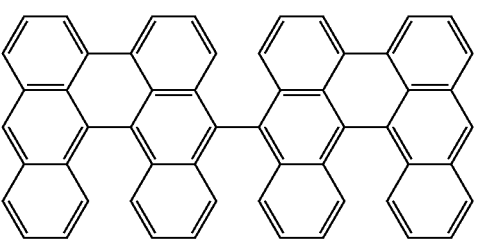

XXII

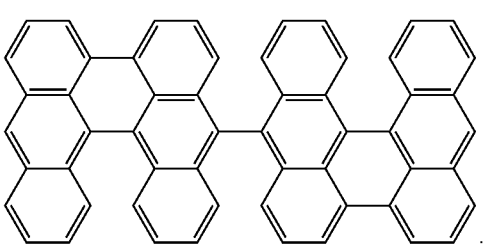

XXIII

10. The method of claim 5, wherein at least one of the one or more polyanthrylenes has a molecular formula of $C_{70}H_{26}$.

11. The method of claim 5, wherein at least one of the one or more polyanthrylenes has a molecular formula of $C_{126}H_{68}$.

12. The method of claim 5, wherein at least one of the one or more polyanthrylenes has a molecular formula of $C_{140}H_{78}$.

13. The method of claim 5, wherein at least one of the one or more polyanthrylenes has a molecular formula of $C_{154}H_{84}$.

14. The method of claim 1, wherein at least one of the one or more polyanthrylenes includes a compound represented by Formula XXIV:

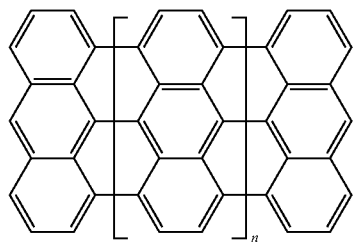

XXIV wherein n is an integer from 1 to 11.

15. The method of claim 1, wherein contacting the sample with the composition to form the mixture comprises contacting the sample with the composition comprising at least at 1 ppm of the one or more polyanthrylenes.

16. The method of claim 1, wherein the mixture exhibits a peak emission wavelength of about 380 nm to about 650 nm when exposed to ultraviolet or violet radiation.

17. The method of claim 1, wherein the average molecular weight of the one or more polyanthrylenes is from about 526 g/mol to about 1932 g/mol.

18. The method of claim 17, wherein the average molecular weight of the one or more polyanthrylenes is from about 526 g/mol to about 868 g/mol.

19. The method of claim 1, wherein the fluorescence produced by exposing the mixture to the radiation is greater in the absence of ferric ions than in the presence of ferric ions.

20. The method of claim 1, wherein the concentration of the ferric ions in the sample is from about $10^{-3}$ M to about $10^{-9}$ M.

21. The method of claim 1, wherein the concentration of the ferric ions in the sample is from about $10^{-6}$ M to about $10^{-9}$ M.

\* \* \* \* \*

UNITED STATES PATENT AND TRADEMARK OFFICE
CERTIFICATE OF CORRECTION

PATENT NO. : 9,063,109 B2
APPLICATION NO. : 14/251396
DATED : June 23, 2015
INVENTOR(S) : Huang et al.

It is certified that error appears in the above-identified patent and that said Letters Patent is hereby corrected as shown below:

In the specification

Column 1, Line 12, delete "§371" and insert -- § 371 --, therefor.

Column 32, Lines 30-42, delete " 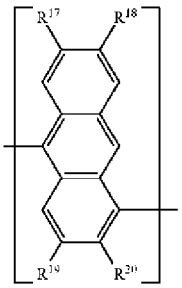 " and insert -- 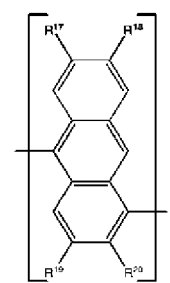 --, therefor.

Column 37, Lines 13-25, delete " 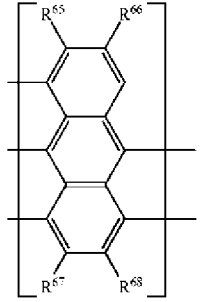 " and insert -- 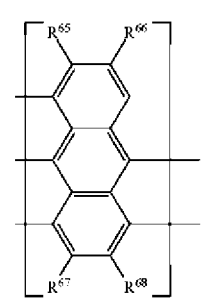 --, therefor.

Column 55, Line 25, delete "lest" and insert -- least --, therefor.

In the claims

Column 61, Line 67, Claim 9, delete "XXIII." and insert -- XXIII: --, therefor.

Signed and Sealed this
Seventeenth Day of May, 2016

Michelle K. Lee
*Director of the United States Patent and Trademark Office*